(12) United States Patent
Liu et al.

(10) Patent No.: US 9,901,566 B1
(45) Date of Patent: Feb. 27, 2018

(54) LIMONOIDS FOR TREATING AUTOIMMUNE DISEASES

(71) Applicant: Macau University of Science and Technology, Taipa (MO)

(72) Inventors: Liang Liu, Taipa (MO); Ting Li, Taipa (MO); Guoyuan Zhu, Taipa (MO); Fen Yang, Taipa (MO)

(73) Assignee: Macau University of Science and Technology, Taipa (MO)

( * ) Notice: Subject to any disclaimer, the term of this patent is extended or adjusted under 35 U.S.C. 154(b) by 0 days.

(21) Appl. No.: 15/401,250

(22) Filed: Jan. 9, 2017

(51) Int. Cl.
*A61K 31/365* (2006.01)

(52) U.S. Cl.
CPC .................. *A61K 31/365* (2013.01)

(58) Field of Classification Search
CPC ................................ A61K 31/365
See application file for complete search history.

(56) References Cited

FOREIGN PATENT DOCUMENTS

AU 2014100777 * 7/2017 ............. C07J 71/00

OTHER PUBLICATIONS

Chen et al. (J. Nat. Prod. 2008, 71, 93-97).*
Y Zhang, X. Y. Luo, D. H. Wu and Y. Xu, "Review: ROR nuclear receptors: structures, related diseases, and drug discovery", Acta Pharmacologica Sinica, vol. 38, pp. 71-87, 2015.
L Battinelli, F Mengoni, M Lichtner, G. Mazzanti, A. Saijam C. M. Mastroianni and V. Vullo, "Effect of limonin and nomilin on HIV-1 replication on infected human monouclear cells", Planta Med., vol. 69, No. 10, pp. 910-913, 2003.
Y. C. Yoon, S. H. Kim, M. J. Kim, H. J. Yang, M. R. Rhyu and J. H Park, "Limonin, a Component of Dictamni Radicis Cortex, Inhibits Eugenol-Induced Calcium and cAMP Levels and PKA/CREB Signaling Pathway in Non-Neuronal 3T3-L1 Cells",. Molecules., vol. 20, pp. 22128-22136, 2015.
A. Zhang, H.Y. Wang, H. Sun, Y. Zhang, N. An, G. Yan, X. Meng and X. Wang, "Metabolomics strategy reveals therapeutical assessment of limonin on nonbacterial prostatitis", Food Funct., vol. 6, pp. 3540-3549, 2015.
S. J. Zunino, D. H. Storms, T. L. Freytag, Y. C. Adkins, E. L. Bonnel, L. R. Woodhouse, A. P. Berksa III, G. D. Manners, B. E. Mackey and D. S. Kelley, "Dietary supplementation with purified citrus limonin glucoside does not alter ex vivo functions of circulating T lymphocytes or monocytes in overweight/obese human adults", Nutr Res., vol. 36, pp. 24-30, 2016.
M. A. Eraky, A. A. El-M. El-Kholy, G. A. El-R. Rashed, O. A. Hammanm, A. F. Moharam, E. A-R. Abou-Ouf, N. S. M. Aly, S. M. Kishik, K. F. Abdallah and D. I. Hamdan, "Dose-response relationship in Schistosoma mansoni juvenile and adult stages following limonin treatment in experimentally infected mice", Parasitol Res., vol. 115, pp. 4045-4054, 2016.

* cited by examiner

*Primary Examiner* — Robert Havlin
(74) *Attorney, Agent, or Firm* — Renner Kenner Greive Bobak Taylor & Weber

(57) ABSTRACT

A method of treating a subject, in particular a human, suffering from an autoimmune disease, preferably but not exclusively selected from systemic lupus erythematosus, multiple sclerosis or rheumatoid arthritis includes the step of administering an effective amount of a limonoid to the subject. The present invention further relates to methods of inhibiting the differentiation of T helper 17 cells, T helper 1 cells, T helper 2 cells and/or regulatory T cells and a method of screening substances for their inhibition of one or more of T helper 17 cell, T helper 1 cell, T helper 2 cell and/or regulatory T cell differentiation that may be used to treat an autoimmune disease. This invention provides highly advantageous and promising treatment options for autoimmune diseases, namely for attenuating inflammatory lymphocyte function.

19 Claims, 22 Drawing Sheets

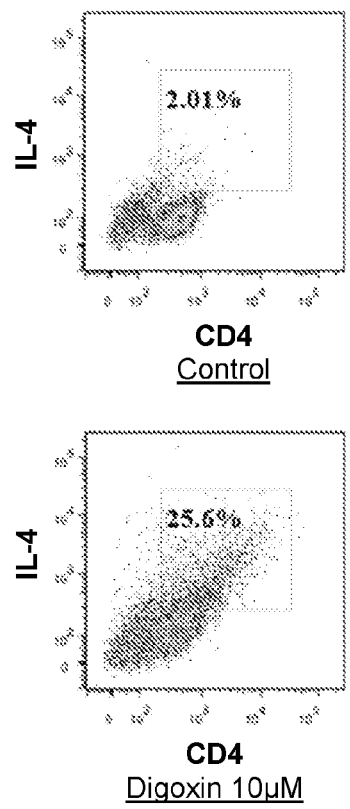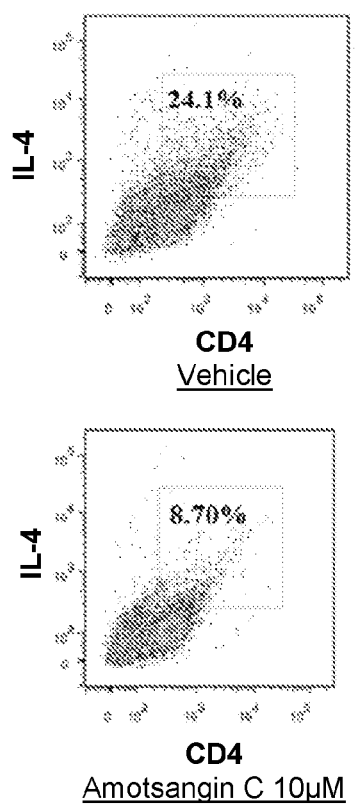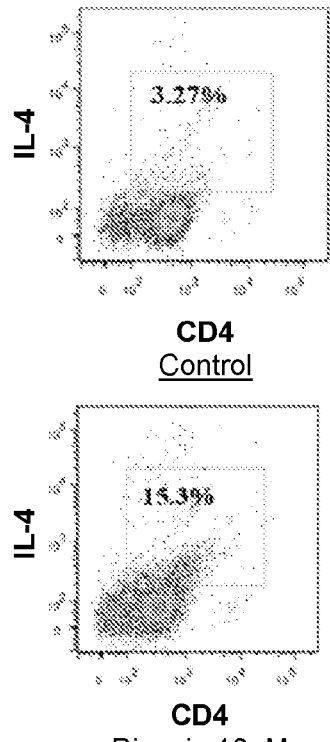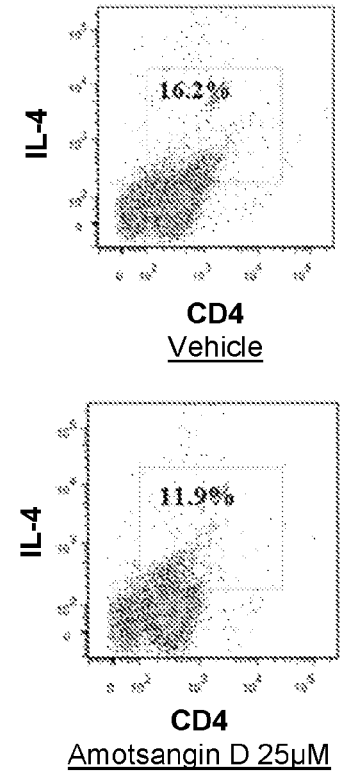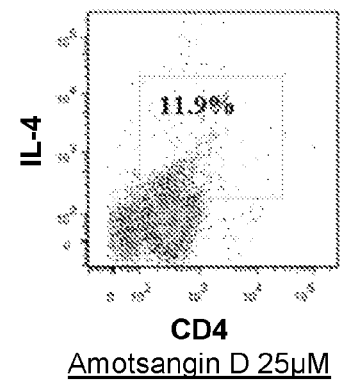
Fig. 6C
Fig. 6D

LIMONOIDS FOR TREATING AUTOIMMUNE DISEASES

TECHNICAL FIELD

The present invention relates to a method of treating a subject, in particular a human, suffering from an autoimmune disease. The autoimmune disease is especially preferably but not exclusively selected from systemic lupus erythematosus, multiple sclerosis or rheumatoid arthritis. Said method comprises the step of administering an effective amount of a limonoid to said subject. The present invention further relates to methods of inhibiting the differentiation of T helper 17 cells, T helper 1 cells, T helper 2 cells and/or regulatory T cells and a method of screening substances for their inhibition of one or more of T helper 17 cell, T helper 1 cell, T helper 2 cells and/or regulatory T cell differentiation that may be used to treat an autoimmune disease.

BACKGROUND OF THE INVENTION

An autoimmune disease occurs when the body's immune system attacks and destroys healthy body tissue. There are as many as 80 types of autoimmune diseases, such as systemic lupus erythematosus (SLE), multiple sclerosis (MS) and rheumatoid arthritis (RA) as common autoimmune diseases in the northern hemisphere affecting an increasing number of patients. Autoimmune diseases are, thus, an enormous global problem that significantly threatens human health. Known treatment options for autoimmune diseases focus on relieving the symptoms as there is no curative therapy available.

There is increasing evidence that auto-reactive T cells contribute to the development of such diseases. Th1, Th2, Th17 and T regulatory (Treg) cells are $CD4^+$ T cell subsets. More specifically, naive $CD4^+$ T cells will differentiate into T helper (Th1, Th2, Th9, Th17) and T regulatory (Treg) cells to execute their functional activities depending on the cytokines in the local environment. They can be characterized by their cytokine profile and by transcription factors. Besides Th1, Th17 are also mainly involved in the progress of autoimmune diseases. Thus, inhibiting IL-17 production has been regarded as a new strategy to treat autoimmune diseases. It is well known the retinoic acid-related orphan nuclear receptor γt (ROR-γt)/RORγ2 is a main regulator of interleukin 17 (IL-17)-producing helper T (Th17) cell development.

Limonin (Limonoate D-ring-lactone) is a member of a group of chemically related triterpene derivatives also known as limonoids found in the Rutaceae and Meliaceae families. It has been reported that Limonin has a broad spectrum of biological activities on insects including insecticidal, insect anti-feedant and growth regulating activity, and it has demonstrated a range of pharmacological properties on humans such as anti-bacterial, anti-fungal, anti-viral, anti-inflammatory and anti-cancer efficiency (Battinelli L. et al., Planta Med. 2003, 69(10): 910-3, Yoon, Y. C. et al., Molecules. 2015, 20(12):22128-36, Breksa, A. P. and Manners, G. D., J Agric Food Chem. 2006, 54(11):3827-31, Zhang, A. et al., Food Funct. 2015, 6(11): 3540-9, Zunino, S. J. et al., Nutr Res. 2016, 36(1):24-30, Eraky, M. A. et al., Parasitol Res. 2016, 115(10): 4045-54).

As the incidence of autoimmune disease is still rising and as treatment options are limited, there remains a strong need for further methods and compounds for treating autoimmune diseases. Such methods should preferably allow for treating such diseases with a reduced risk of side effects. Respective compounds should be easily obtainable.

SUMMARY OF THE INVENTION

The first aspect of the present invention relates to a method of treating a subject, in particular a human, suffering from an autoimmune disease. Said method comprises the step of administering an effective amount of a limonoid to said subject. The limonoid used in the method of the present invention comprises a structure of Formula (I):

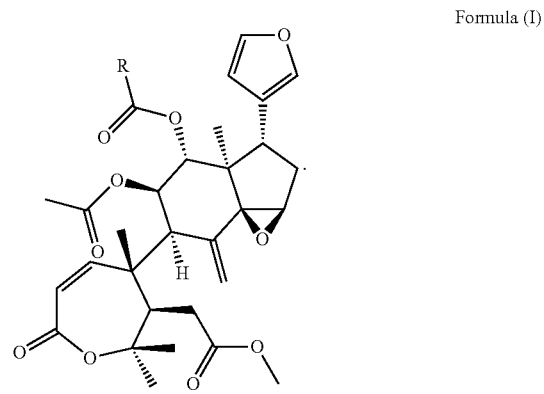

Formula (I)

R is selected from an optionally hydroxylated alkyl group.

The limonoid in particular comprises a structure selected from one of Formulas (II) to (V):

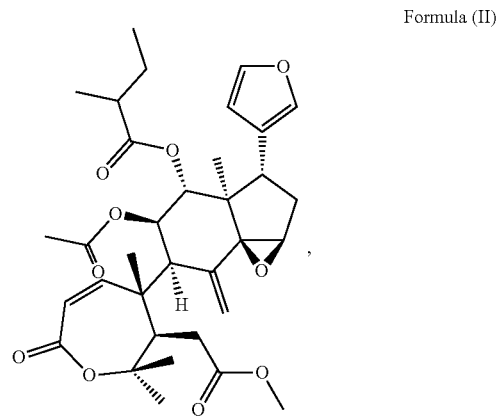

Formula (II)

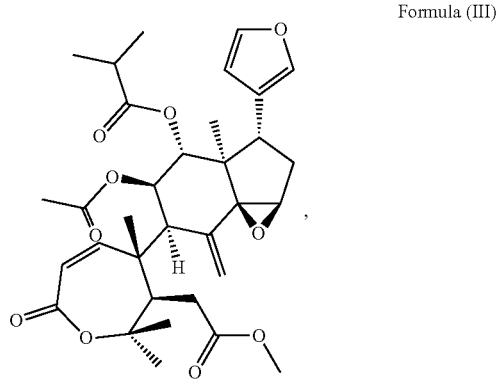

Formula (III)

-continued

Formula (IV)

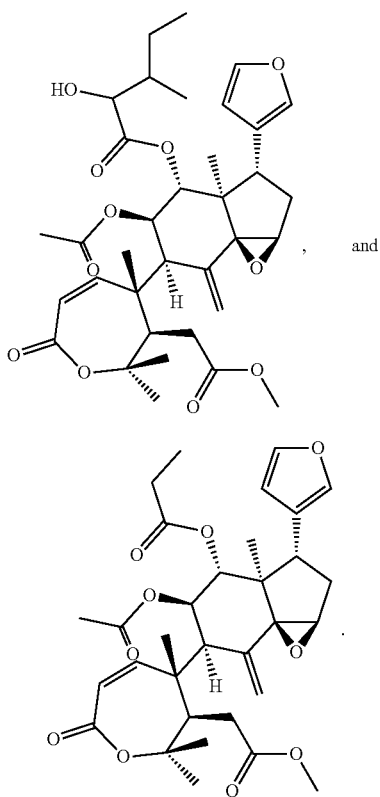

, and

Formula (V)

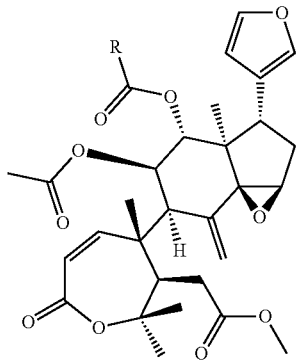

The method of the present invention in particular includes inhibiting the T helper cell and/or regulatory T cells differentiation from naive CD4+ T cells, i.e. the limonoid inhibits T helper cell and/or regulatory T cell differentiation.

The present invention in another aspect relates to a method of inhibiting the differentiation of T helper 17 cells. Said method comprises contacting naive CD4+ T cells with an effective amount of a limonoid. Said limonoid comprises a structure of Formula (I):

Formula (I)

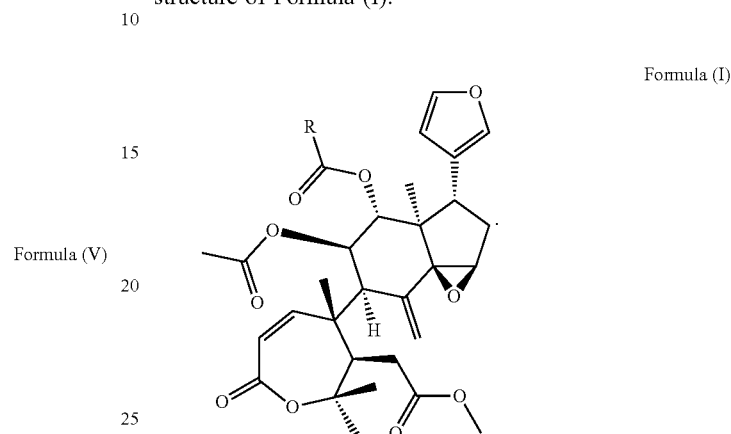

R is selected from an optionally hydroxylated alkyl group.

The limonoid in particular reduces the ROR-γt protein expression, i.e. the method of inhibiting the differentiation of T helper 17 cells of the present invention includes reducing the ROR-γt protein expression. Alternatively or additionally, the limonoid in particular reduces the IL-17 production, i.e. the method of inhibiting the differentiation of T helper 17 cells of the present invention includes reducing the IL-17 production.

The present invention is another aspect refers to a method of inhibiting the differentiation of one or more of T helper 1 cells, T helper 2 cells or regulatory T cells. Said method comprises contacting naive CD4+ T cells with an effective amount of a limonoid, wherein the limonoid comprises a structure of Formula (I):

Formula (I)

R is selected from an optionally hydroxylated alkyl group.

The limonoid in particular reduces one or more of the INF-γ production, the IL-4 production and/or the Foxp3 production, i.e. the method of inhibiting the differentiation of one or more of T helper 1 cells, T helper 2 cells or regulatory T cells includes reducing one or more of the INF-γ production, the IL-4 production and/or the Foxp3 production.

In another aspect, the present invention provides a method of screening substances for their inhibition of one or more of T helper 17 cell, T helper 1 cell, T helper 2 cell and/or regulatory T cell differentiation that may be used to treat an autoimmune disease, which method comprises steps of:

(i) subjecting the substance to an assay;
(ii) detecting whether the substance inhibits one or more of T helper 17 cell, T helper 1 cell, T helper 2 cell and/or regulatory T cell differentiation.

The methods of the present invention provide highly advantageous and promising treatment options for autoimmune diseases, namely for attenuating inflammatory lymphocyte function. In particular, the inventors unexpectedly found that the limonoids Amotsangin A, B, C and D are able to suppress T helper 17 (Th17) cell differentiation from CD4+ T splenocytes of mice without cytotoxicity. Amotsangin A, B, C and D proved to be able to inhibit Th17 differentiation through reducing ROR-γt luciferase activity reporter and reducing ROR-γt protein expression. The inventors further found an additional inhibitory effect of Amotsangin B and C on the T helper 1 cell differentiation, Amotsangin B, C and D on the T helper 2 cell differentiation and Amotsangin C on the regulatory T cell differentiation which was confirmed by a reduction of respective markers INF-γ, IL-4 and/or Foxp3.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF THE DRAWINGS

FIG. 1A shows the cell viability of PBMCs treated with 5 μM, 10 μM, 25 μM and 50 μM Amotsangin A. FIG. 1B shows the cell viability of PBMCs treated with 5 μM, 10 μM, 25 μM and 50 μM Amotsangin B. FIG. 1C shows the cell viability of PBMCs treated with 1 μM, 5 μM, 10 μM and 25 μM Amotsangin C. FIG. 1D shows the cell viability of PBMCs treated with 5 μM, 10 μM, 25 μM and 50 μM Amotsangin D. Data represent mean±SEM (n=3). Statistically significant differences with respect to the Control is expressed as *$P<0.05$; $P<0.01$; *$P<0.001$.

FIG. 2A is a diagram showing the dose-dependent inhibitory effect of Amotsangin A on ROR-γt luciferase reporter activity at concentrations of 5 μM, 10 μM, 25 μM and 50 μM. FIG. 2B is a diagram showing the dose-dependent inhibitory effect of Amotsangin B on ROR-γt luciferase reporter activity at concentrations of 5 μM, 10 μM, 25 μM and 50 μM. FIG. 2C is a diagram showing the dose-dependent inhibitory effect of Amotsangin C on ROR-γt luciferase reporter activity at concentrations of 1 μM, 5 μM, 10 μM and 25 μM. FIG. 2D is a diagram showing the dose-dependent inhibitory effect of Amotsangin D on ROR-γt luciferase reporter activity at concentrations of 5 μM, 10 μM, 25 μM and 50 μM. Statistically significant differences with respect to the Control is expressed as $P<0.01$; *$P<0.001$.

FIG. 3A shows the blotted protein band patterns of protein ROR-γt and β-actin as reference control which HEK293 cells were treated with 5 μM, 10 μM, 25 μM and 50 μM Amotsangin A. FIG. 3B shows the blotted protein band patterns of protein ROR-γt and β-actin as reference control which HEK293 cells were treated with 5 μM, 10 μM, 25 μM and 50 μM Amotsangin B. FIG. 3C shows the blotted protein band patterns of protein ROR-γt and β-actin as reference control which HEK293 cells were treated with 1 μM, 5 μM, 10 μM and 25 μM Amotsangin C. FIG. 3D shows the blotted protein band patterns of protein ROR-γt and β-actin as reference control which HEK293 cells were treated with 5 μM, 10 μM, 25 μM and 50 μM Amotsangin D.

FIG. 4A shows the flow cytometry patterns of control group, vehicle group and treatment groups which cells were untreated or treated with 10 μM digoxin, and 5 μM, 10 μM and 25 μM Amotsangin A. FIG. 4B shows the flow cytometry patterns of control group, vehicle group and treatment groups which cells were untreated or treated with 10 μM digoxin, and 5 μM, 10 μM and 25 μM Amotsangin B. FIG. 4C shows the flow cytometry patterns of control group, vehicle group and treatment groups which cells were untreated or treated with 10 μM digoxin, and 1 μM, 5 μM and 10 μM Amotsangin C. FIG. 4D shows the flow cytometry patterns of control group, vehicle group and treatment groups which cells were untreated or treated with 10 μM digoxin, and 5 μM, 10 μM and 25 μM Amotsangin D. FIG. 4E to 4H are diagrams showing the effect of Amotsangin A, Amotsangin B, Amotsangin C or Amotsangin D on IL-17 production. Statistically significant differences with respect to the Vehicle is expressed as *$P<0.05$; $P<0.01$; *$P<0.001$.

FIG. 5A shows the flow cytometry patterns of control group, vehicle group and treatment groups which cells were untreated or treated with 10 μM digoxin, and 25 μM Amotsangin A. FIG. 5B shows the flow cytometry patterns of control group, vehicle group and treatment groups which cells were untreated or treated with 10 μM digoxin, and 25 μM Amotsangin B. FIG. 5C shows the flow cytometry patterns of control group, vehicle group and treatment groups which cells were untreated or treated with 10 μM digoxin, and 10 μM Amotsangin C. FIG. 5D shows the flow cytometry patterns of control group, vehicle group and treatment groups which cells were untreated or treated with 10 μM digoxin, and 25 μM Amotsangin D. FIG. 5E to 5H are diagrams showing the effect of Amotsangin A, Amotsangin B, Amotsangin C or Amotsangin D on IFN-γ production. Statistically significant differences with respect to the Vehicle is expressed as ***$P<0.001$.

FIGS. 6A through 6H show the IL-4 production and Th2 differentiation by flow cytometry. CD4$^+$ T cells isolated from the spleens of C57BL/6 mice were cultured under Th2-polarizing conditions in the presence or absence of digoxin, or Amotsangin A, Amotsangin B, Amotsangin C or Amotsangin D. FIG. 6A shows the flow cytometry patterns of control group, vehicle group and treatment groups which cells were untreated or treated with 10 μM digoxin, and 25 μM Amotsangin A. FIG. 6B shows the flow cytometry patterns of control group, vehicle group and treatment groups which cells were untreated or treated with 10 μM digoxin, and 25 μM Amotsangin B. FIG. 6C shows the flow cytometry patterns of control group, vehicle group and treatment groups which cells were untreated or treated with 10 μM digoxin, and 10 μM Amotsangin C. FIG. 6D shows the flow cytometry patterns of control group, vehicle group and treatment groups which cells were untreated or treated with 10 μM digoxin, and 25 μM Amotsangin D. FIG. 6E to 6H are diagrams showing the effect of Amotsangin A, Amotsangin B, Amotsangin C or Amotsangin D on IL-4 production. Statistically significant differences with respect to the Vehicle is expressed as *$P<0.05$; ***$P<0.001$.

FIG. 7A shows the flow cytometry patterns of control group, vehicle group and treatment groups which cells were untreated or treated with 10 μM digoxin, and 25 μM Amotsangin A. FIG. 7B shows the flow cytometry patterns of control group, vehicle group and treatment groups which cells were untreated or treated with 10 μM digoxin, and 25 μM Amotsangin B. FIG. 7C shows the flow cytometry patterns of control group, vehicle group and treatment groups which cells were untreated or treated with 10 μM digoxin, and 10 μM Amotsangin C. FIG. 7D shows the flow cytometry patterns of control group, vehicle group and treatment groups which cells were untreated or treated with 10 μM digoxin, and 25 μM Amotsangin D. FIG. 7E to 7H are diagrams showing the effect of Amotsangin A, Amotsangin B, Amotsangin C or Amotsangin D on IL-4 production.

DETAILED DESCRIPTION OF THE INVENTION

Figure 1A:
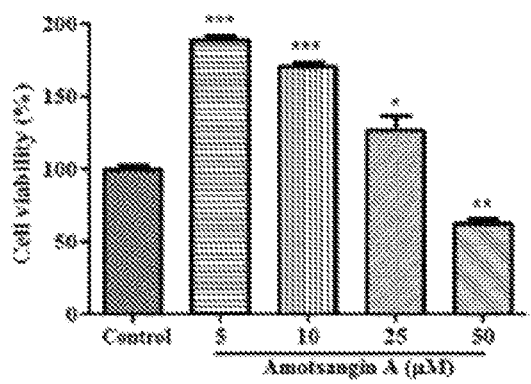
FIGS. 1A through 1D show the cell viability of human peripheral blood mononuclear cells (PBMCs) treated with different concentration of Amotsangin A, Amotsangin B, Amotsangin C and Amotsangin D via MTT analysis.
Figure 1B:
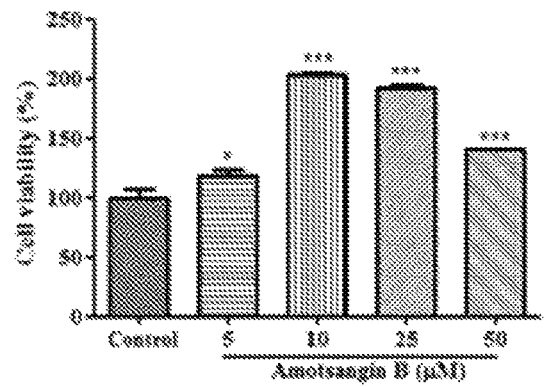
Figure 1C:
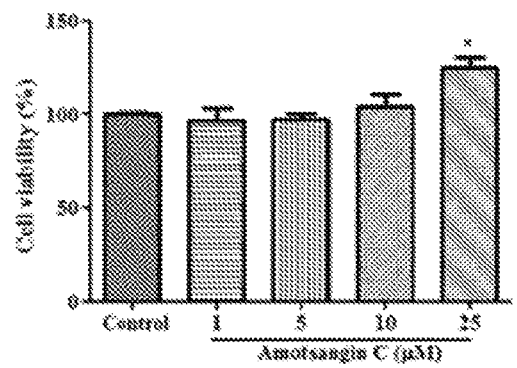
Figure 1D:
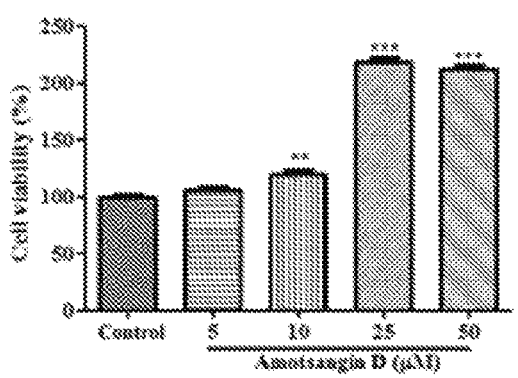
Figure 2A:
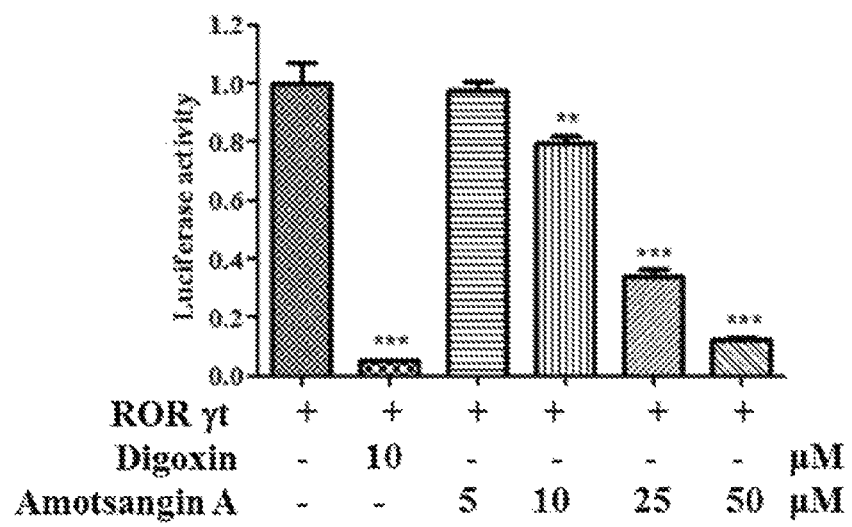
FIGS. 2A through 2D show the effect of Amotsangin A, Amotsangin B, Amotsangin C and Amotsangin D on ROR-γt luciferase reporter activity via Lightswitch Luciferase assay.
Figure 2B:
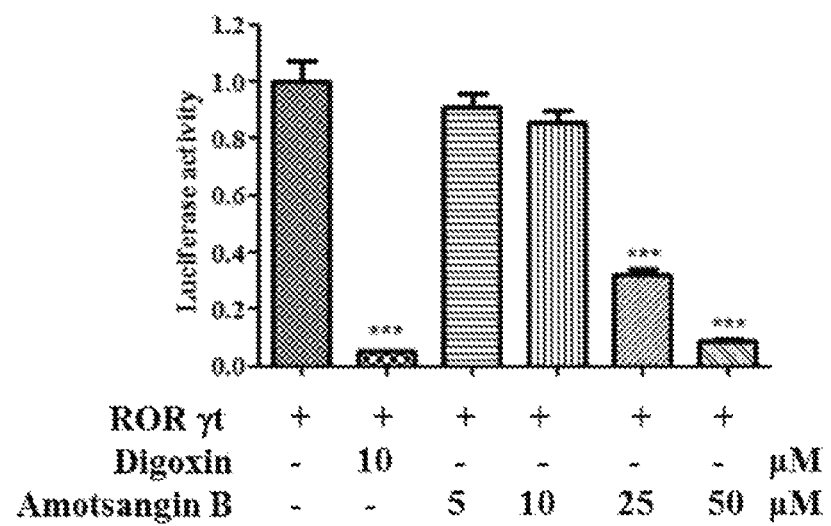
Figure 2C:
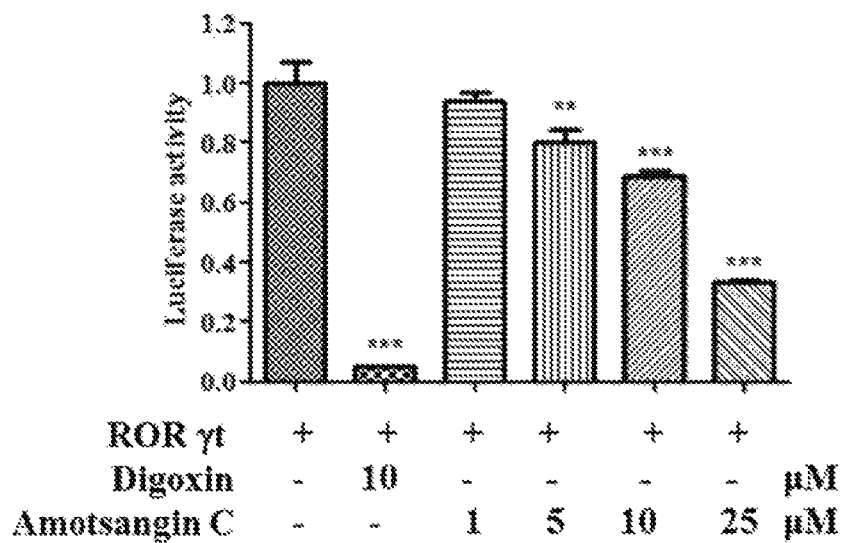
Figure 2D:
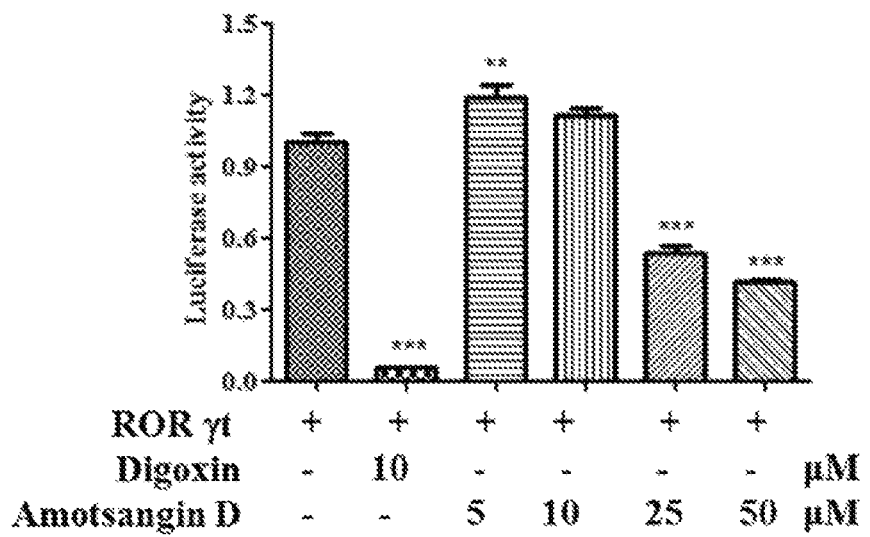

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. The expression that a material "is" certain element as used herein means that the material essentially consists of said element. As used herein, the forms "a," "an," and "the," are intended to include the singular and plural forms unless the context clearly indicates otherwise.

The present invention provides a method for treating a subject suffering from an autoimmune disease. Said method comprises the step of administering an effective amount of a limonoid to said subject.

Limonoids are generally known as highly oxygenated and modified terpenoids with a prototypical structure either containing or derived from a 4,4,8-trimethyl-17-furanyl-steroid skeleton usually with a furan-ring attached to the D ring:

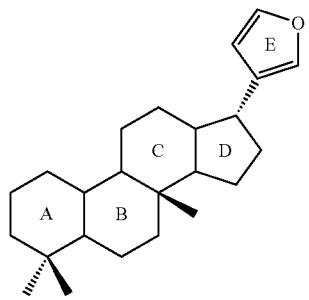

They can be found in citrus fruits and other plants in particular of the families Rutaceae and Meliaceae.

The limonoid used in the method of the present invention comprises a structure of Formula (I):

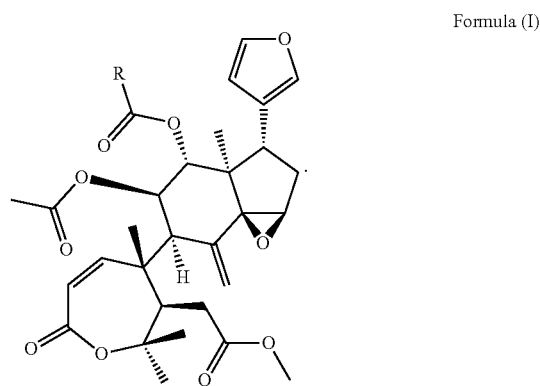

Formula (I)

R is selected from an optionally hydroxylated alkyl group.

The term "alkyl group" as used in the present invention refers to a straight chain or branched hydrocarbyl radical comprising carbon and hydrogen atoms. Accordingly, "$C_1$-$C_5$ alkyl group" refers to a hydrocarbyl radical comprising from 1 to 5 carbon atoms and "$C_2$-$C_5$ alkyl group" refers to a hydrocarbyl radical comprising from 2 to 5 carbon atoms. "Straight chain or branched alkyl" includes all linear or branched alkyl groups. For example, $C_1$-$C_5$ alkyl group includes methyl, ethyl, n-propyl, isopropyl, butyl and its isomers (e.g. n-butyl, isobutyl, sec-butyl and tert-butyl), pentyl and its isomers (n-pentyl, tert-pentyl neopentyl, iso-pentyl, sec-pentyl, 3-pentyl). The alkyl group is preferably a $C_1$-$C_5$ alkyl group, further preferred a $C_2$-$C_5$ alkyl group.

The term "optionally hydroxylated alkyl group" means an alkyl group which optionally has one or more hydroxyl groups (—OH) attached to one or more carbon atom of the alkyl group, in particular one hydroxyl group attached to one carbon atom of the alkyl group.

R is preferably selected from an optionally hydroxylated $C_1$-$C_5$ alkyl group, more preferably an optionally hydroxylated $C_2$-$C_5$ alkyl group.

Still more preferably, R is selected from one of ethyl, 2-butyl, iso-propyl or 1-hydroxy-2-methyl-butyl.

I.e. R is more preferably selected from one of

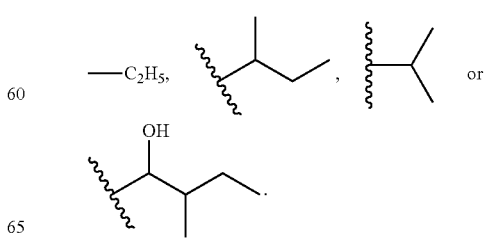

Most preferably, the limonoid comprises a structure selected from one of Formulas (II) to (V):

Formula (II)

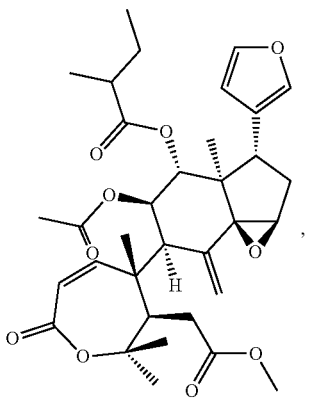

,

Formula (III)

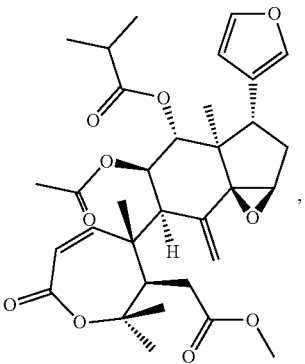

,

Formula (IV)

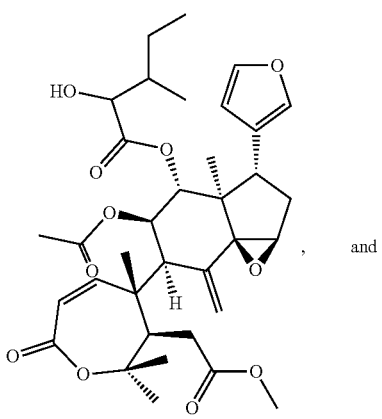

, and

Formula (V)

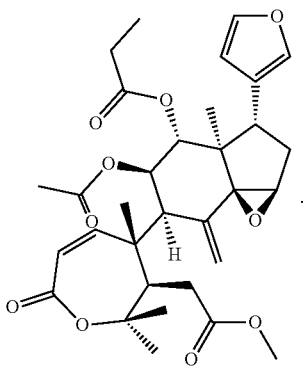

In especially preferred embodiments of the method of the present invention, the limonoid consists of a structure of one or more of Formulas (II) to (V), i.e. is selected from Amotsangin A (Formula (II)), Amotsangin B (Formula (III)), Amotsangin C (Formula (IV) or Amotsangin D (Formula (V)) or a mixture of two, three or all of them. Said limonoids are commercially available and/or can be extracted from plants such as from the Rutaceae and Meliaceae family, for example, from *Amoora tsangii* such as by an extraction. One of skill in the art is aware of suitable methods for obtaining limonoids from plants such as extraction with ethanol, followed by partitioning between ethyl acetate and water to give an ethyl acetate soluble fraction and fractionating said fraction including chromatography.

"Autoimmune disease" as used herein refers to disorders resulting from an immune response against the subject's own tissue or tissue components or to antigens that are not intrinsically harmful to the subject. The symptoms and degree of severity can vary. The term encompasses organ-specific autoimmune diseases and non-organ specific autoimmune diseases such as type I diabetes mellitus, Crohn's disease, ulcerative colitis, myasthenia gravis, Hashimoto's disease, Addison's disease and autoimmune gastritis and autoimmune hepatitis, rheumatoid arthritis, systemic lupus erythematosus, progressive systemic sclerosis, polymyositis and dermatomyositis, multiple sclerosis and psoriasis. One of skill in the art will understand that the methods of the invention can also be applied to other autoimmune diseases. In particular embodiments of the present invention, the autoimmune disease is selected from the group consisting of systemic lupus erythematosus, multiple sclerosis and rheumatoid arthritis.

The term "subject" used herein refers to a living organism and can include but is not limited to a human and an animal. The subject is preferably a mammal, more preferably a human.

The limonoid of the present invention can be present in solid, semisolid or liquid form. The limonoid of the present invention can be administered by an oral or parenteral route to the subject, in particular by an oral route or an intravenous route.

The limonoid of the present invention may be administered in form of a pharmaceutical composition comprising said limonoid and a pharmaceutically tolerable excipient such as selected from a pharmaceutically tolerable carrier, salt, buffer, water, diluent, a filler, a binder, a disintegrant, a lubricant, a coloring agent, a surfactant or a preservative or a combination thereof. A person of skill in the art is able to select suitable pharmaceutically tolerable excipients depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition. The pharmaceutical composition can be present in solid, semisolid or liquid form to be administered by an oral or parenteral route to the subject.

In an embodiment, the limonoid of the present invention can be used as a single compound for treating the subject in particular with autoimmune disease.

In other embodiments, the limonoid of the present invention is administered in combination with other therapeutically effective treatments such as other compounds used for treating autoimmune diseases.

The expression "effective amount" and "effective dose" generally denote an amount sufficient to produce therapeutically desirable results, wherein the exact nature of the result varies depending on the specific disorder which is treated. When the disorder is an autoimmune disease, the result is usually a reduction of the inflammation such as a reduction of inflammatory markers.

The effective amount of the limonoid of the present invention may depend on the species, body weight, age and individual conditions of the subject and can be determined by standard procedures such as with cell cultures or experimental animals.

The method of the present invention preferably includes inhibiting the T helper cell and/or regulatory T cells differentiation from naive CD4$^+$ T cells, i.e. the limonoid inhibits T helper cell and/or regulatory T cells differentiation.

The term "inhibiting" cell differentiation as used herein for the T helper 17 (Th17), T helper 1 (Th1), T helper 2 (Th2) and regulatory T cells (Tregs) differentiation includes any kind of reduction, suppression and in particular a prevention of said cell differentiation. In particular, inhibiting T helper cell and/or regulatory T cells differentiation as used herein means one or more of a reduction, in particular a significant reduction in:

- the ROR-γt protein expression as marker for a reduced differentiation into Th17 cells;
- the IL-17 production as marker for a reduced differentiation into Th17 cells;
- the INF-γ production as marker for a reduced differentiation into Th1 cells;
- the IL-4 production as marker for a reduced differentiation into Th2 cells; and/or
- the Foxp3 production as marker for a reduced differentiation into regulatory Tregs.

Further preferred, a reduction of IL-17 production, INF-γ production, IL-4 production and/or Foxp3 production means that the amount of cells with a production of IL-17, INF-γ, IL-4 or Foxp3 is reduced by at least 3 percentage points, in particular by at least 5 percentage points, further preferred by at least 7 percentage points and in particular by at least 8 percentage points under the treatment with a limonoid of the present invention compared to a reference group without limonoid treatment in particular as determined with flow cytometry assay. A reduction in ROR-γt protein expression preferably means a reduction in the expressed amount of ROR-γt under the treatment with the limonoid of the present invention by at least about 10%, further preferred by at least about 30% which can be determined by means of Western blotting compared to a reference group without treatment. Alternatively, luciferase reporter assays or ELISA assays may be used. In particular, the reduction in ROR-γt protein expression can mean a reduction in a luciferase activity measured with a luciferase reporter assay by at least 30%, in particular by at least 50% compared to a reference group without limonoid treatment.

The limonoid in particular reduces the ROR-γt protein expression, i.e. the method of the present invention includes reducing the ROR-γt protein expression.

Alternatively or additionally, the limonoid in particular reduces the IL-17 production, i.e. the method of the present invention includes reducing the IL-17 production.

The present invention in another aspect relates to a method of inhibiting the differentiation of T helper 17 cells. Said method comprises contacting naive CD4$^+$ T cells with an effective amount of a limonoid. Said limonoid comprises a structure of Formula (I):

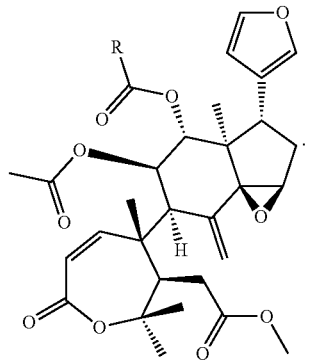

Formula (I)

R is selected from an optionally hydroxylated alkyl group.

The term "CD4$^+$ T cells" refers to lymphocytes that produce the CD4 protein. Such CD4$^+$ T cells include cells isolated from natural sources such as blood, cell lines grown in culture. Typically, a CD4$^+$ T cell according to the invention is a human CD4$^+$ T cell. As used herein, the term "naive CD4$^+$ T cells" refers to a CD4$^+$ T cell that is functionally defined by the expression of cell surface markers of naivety. They can be activated after antigenic stimulation and differentiate into specific subtypes depending mainly on the cytokine milieu of the microenvironment including Th1, Th2, Th17 and Treg cells.

The step of contacting the naive CD4$^+$ T cells with the limonoid of the present invention preferably includes the administration of the limonoid of the present invention to a subject having the naive CD4$^+$ T cells, in particular a subject having an autoimmune disease. The step of contacting the naive CD4$^+$ T cells with the limonoid of the present invention alternatively includes applying an incubation solution comprising the naive CD4$^+$ T cells with the limonoid of the present invention to said cells which incubation solution may further comprise suitable excipients such as buffers or a suitable growth medium.

The method may further comprise contacting said naive CD4$^+$ T cells with a further compound such as another compound used for treatment of autoimmune diseases.

The naive CD4$^+$ T cells may be contacted with the limonoid of the present invention for at least about 24 h.

The limonoid in particular reduces the ROR-γt protein expression, i.e. the method of inhibiting the differentiation of T helper 17 cells of the present invention includes reducing the ROR-γt protein expression.

Alternatively or additionally, the limonoid in particular reduces the IL-17 production, i.e. the method of inhibiting the differentiation of T helper 17 cells of the present invention includes reducing the IL-17 production.

The naive CD4$^+$ T cells are preferably contacted with the limonoid of the present invention in a concentration of about 1 μM to about 50 μM. The concentration of the limonoid is preferably between about 1 μM and about 25 μM and can be between about 1 μM and about 10 μM. If the limonoid comprises or in particular consists of a structure of one of Formulas (II), (III) or (V), the concentration is preferably about 5 μM to about 25 μM.

If the limonoid comprises or consists of a structure of Formula (IV), the concentration is preferably about 1 μM to about 10 μM.

More preferably, the limonoid for contacting the naive CD4$^+$ T cells comprises a structure selected from one of Formulas (II) to (V):

Formula (II)

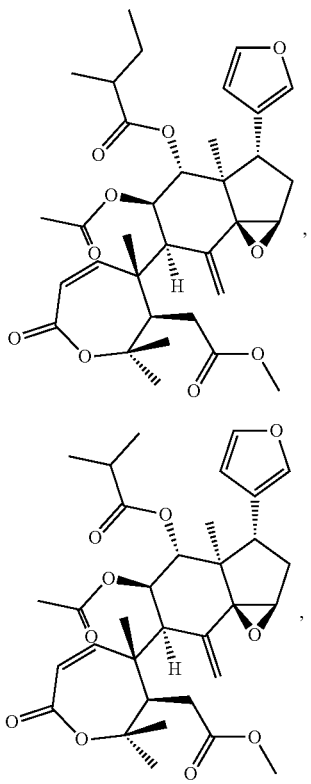

Formula (III)

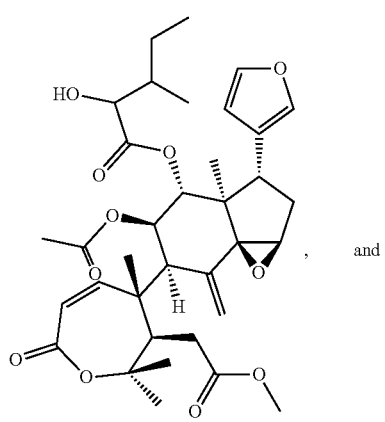

Formula (IV)

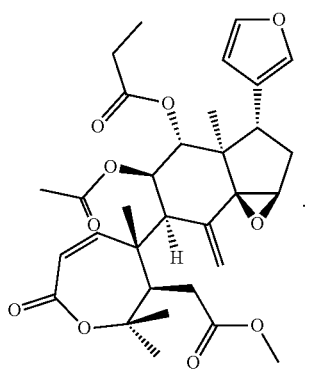

Formula (V)

Most preferably, the limonoid used for contacting the naive CD4+ T cells comprises a structure of Formula (II):

Formula (II)

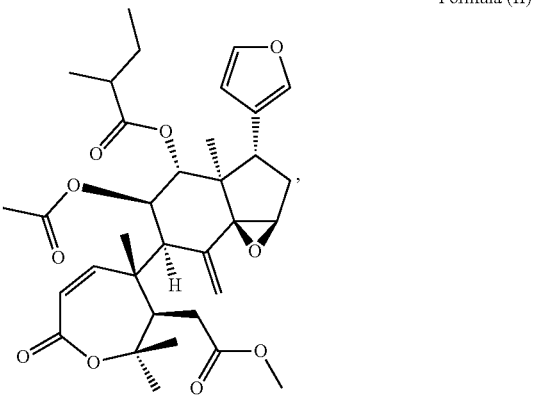

and is used in a concentration of between about 5 μM and about 50 μM, in particular, the limonoid consists of a structure of Formula (II), i.e. is Amotsangin A.

The present invention in another aspect refers to a method of inhibiting the differentiation of one or more of T helper 1 cells, T helper 2 cells or regulatory T cells. Said method comprises contacting naive CD4+ T cells with an effective amount of a limonoid, wherein the limonoid comprises a structure of Formula (I):

Formula (I)

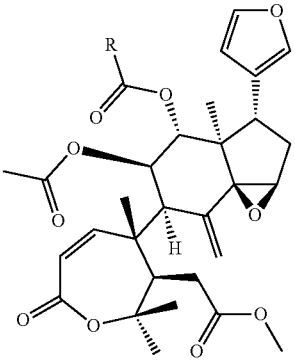

R is selected from an optionally hydroxylated alkyl group.

The limonoid in particular reduces one or more of the INF-γ production, the IL-4 production and/or the Foxp3 production, i.e. the method of inhibiting the differentiation of one or more of T helper 1 cells, T helper 2 cells or regulatory T cells includes reducing one or more of the INF-γ production, the IL-4 production and/or the Foxp3 production.

In preferred embodiments of the method of the present invention, the differentiation of the T helper 1 cells is inhibited and the limonoid comprises a structure of one of Formulas (III) or (IV):

Formula (III)

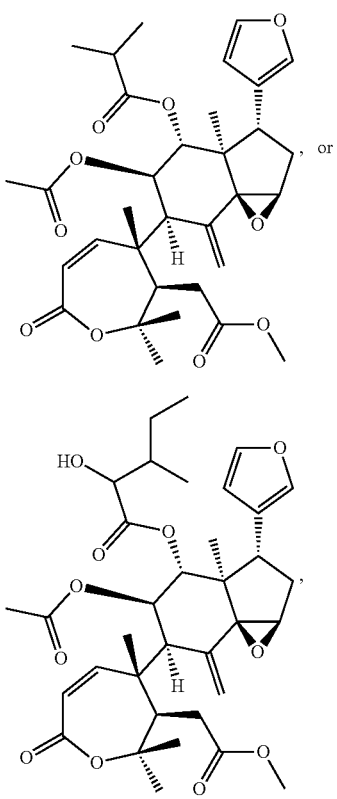

Formula (IV)

and the limonoid is used in a concentration of about 10 μM to about 25 μM.

In particular embodiments, the limonoid consists of a structure of one of Formulas (III) or (IV), i.e. is Amotsangin B or Amotsangin C or is a mixture of both.

The limonoid comprising or preferably consisting of a structure of Formula (III) is preferably used in a concentration of about 25 μM.

The limonoid comprising or preferably consisting of a structure of Formula (IV) is preferably used in a concentration of about 10 μM.

In other embodiments of the method of the present invention, the differentiation of T helper 2 cells is inhibited and the limonoid comprises a structure of one of Formulas (III), (IV) or (V):

Formula (III)

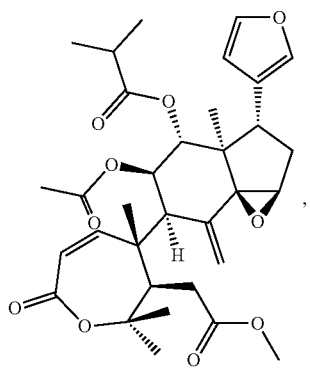

Formula (IV)

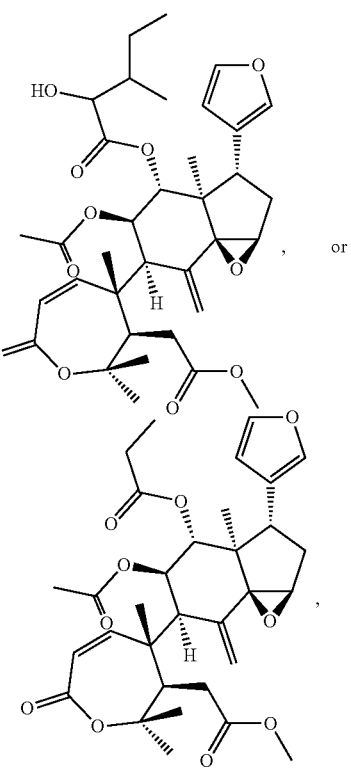

Formula (V)

and the limonoid is used in a concentration of between about 10 μM and about 25 μM.

In particular embodiments, the limonoid consists of a structure of one of Formulas (III), (IV) or (V), i.e. is Amotsangin B, Amotsangin C or Amotsangin D or is a mixture thereof.

The limonoid comprising or preferably consisting of a structure of Formula (III) is preferably used in a concentration of about 25 μM.

The limonoid comprising or preferably consisting of a structure of Formula (IV) is preferably used in a concentration of about 10 μM.

The limonoid comprising or preferably consisting of a structure of Formula (V) is preferably used in a concentration of about 25 μM.

In other embodiments of the method of the present invention, the differentiation of regulatory T cells is inhibited and the limonoid comprises a structure of Formula (IV)

Formula (IV)

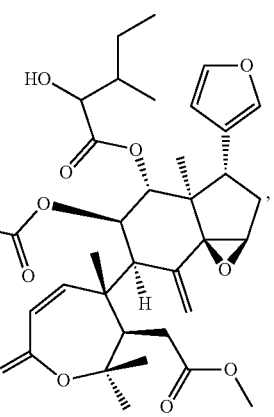

and the limonoid is used in a concentration of about 10 µM.

In particular embodiments, the limonoid consists of a structure of Formula (IV), i.e. is Amotsangin C.

In another aspect, the present invention provides a method of screening substances for their inhibition of one or more of the Th17, Th1, Th2 and/or Treg cell differentiation that may be used to treat an autoimmune disease, which method comprises steps of:

(i) subjecting the substance to an assay;

(ii) detecting whether the substance inhibits one or more of the Th17, Th1, Th2 and/or Treg cell differentiation.

Said inhibition of cell differentiation can be detected in step (ii) by one or more of: determining whether a marker for the respective T cell differentiation is reduced, whether ROR-γt luciferase activity is reduced and/or whether ROR-γt protein expression or activity is reduced.

For example, the method of screening may comprise steps of:

(i) subjecting the substance to an assay comprising ROR-γt;

(ii) detecting whether the substance reduces the activity or protein expression of ROR-γt.

EXAMPLES

Example 1

Cytotoxicity of Amotsangin A, B, C and D as Limonoids of the Present Invention

The cell viability of human peripheral blood mononuclear cells (PBMCs) under treatment with Amotsangin A, B, C and D has been evaluated Isolation and Cultures of Human PBMCs Human peripheral blood mononuclear cells have been isolated from buffy coat. In brief, the buffy coat provided by Macao Blood Transfusion Centre was mixed with normal saline, and then added to 50 mL centrifuge tube containing Ficoll-Pague plus (Amersham Biosciences). The mixture was separated into several layers after centrifuged at 350 g for 35 min. The layer of mononuclear cells has been collected, and then washed twice by normal saline. These cells were be used for the experiments.

Cell Viability Assay

Human PBMCs ($1 \times 10^5$/well) were cultured in 96-well plates in triplicate in RPMI 1640 medium (Gibco, Paisley, UK) with 10% fetal bovine serum (FBS; Gibco), penicillin (100 units/mL) and streptomycin (100 µg/mL), and different concentration of Amotsangin A, B, C and D were added for 72 h. MTT (5 mg/mL) was added to the cells followed by 4 h incubation, followed by addition of solvent (10% sodium dodecyl sulfate (SDS), 50% N, N-dimethyl formamide, pH 7.2) to dissolve the purple precipitate. The absorbance was recorded on a Microplate UV/VIS Spectrophotometer (TECAN, Switzerland) at 570 nm wavelength on the following day. The percentage of cell viability was calculated using the following formula: Cell viability (%)=($OD_{treated}-OD_{blank}$)/($OD_{control}-OD_{blank}$)×100.

Results

Amotsangin A, B, C and D had no significant cytotoxicity on human PBMCs, even if used in a concentration of up to 50 µM. The results are shown in FIG. 1.

Example 2

Effects of Amotsangin A, B, C and D as Limonoids of the Present Invention on the ROR-γt Luciferase Reporter Activity Lightswitch Luciferase Reporter Assay ROR Gamma T LUCPorter™ Stable Reporter cells and LUCPorter™ Vector Control HEK293 cells (Imgenex) were plated in 96-well plates at $5 \times 10^4$ cells/well in triplicate in RPMI 1640 medium with 10% fetal bovine serum, penicillin (100 units/mL), streptomycin (100 µg/mL) and puromycin (3 µg/mL) over night. Cells were treated with 5, 10, 25, and 50 µM Amotsangin A, B, C or D or 10 µM digoxin for 16 h. Then the complete mixture of luciferase assay reagent (Biocompare, Texas, USA) has been added to the wells and the mixture has been incubated for 30 min at room temperature in the dark. The mixture has been transferred into a 96 well white plates before reading. Finally, each well was read for 2 seconds in a plate luminometer on a Microplate UV/VIS Spectrophotometer (TECAN, Switzerland). Data are obtained from three independent experiments.

Results

Amotsangin A, B and D dose-dependently reduced ROR-γt luciferase reporter activity when used in concentrations of from 5 to 50 µM, while Amotsangin C dose-dependently reduced ROR-γt luciferase reporter activity when used in concentrations of from 1 to 25 µM as shown in FIG. 2.

Example 3

Effects of Amotsangin A, B, C and D as Limonoids of the Present Invention on the Expression of ROR-γt in HEK293 Cells Transfection of Human ROR-γt Plasmid to a HEK293 Cell Line The transfection assay is preformed according to the manufacturer's instruction of lipofectamine LTX (invitrogen, USA). In brief, HEK293 cells obtained from the American Type Culture Collection (ATCC, Manassas, Va., USA) were seeded in 1.5 ml of DMEM growth media plus 10% FBS at $5 \times 10^5$ cells per well. Five hundred micro liter Opti-MEM Reduced Serum Media containing 1.25 µg of DNA was added to the cells to be transfected, and then 1.25 µl of PLUS was added into the above diluted Opti-MEM: DNA solution, gently mixed and incubated for another 5 min at room temperature. Subsequently, lipofectamine LTX™ Reagent was added into the above solution, mixed gently and then incubated 30 min at room temperature to form DNA-lipofectamine LTX Reagent complexes. Finally, 500 µl of the DNA-lipofectamine LTX Reagent complexes was directly added to each well containing cells and mixed gently. The cells were incubated at 37° C. in a CO$_2$ incubator for another 24 h.

Western Blotting Assay

After incubated for 24 h, the transfected HEK293 cells were treated with different concentrations of Amotsangin A, B, C or D for another 24 h. Then the cells were lysed with RIPA buffer containing 1× protease inhibitor mix (Roche, USA) to harvest total cellular proteins, and the protein concentration was calculated by the bicinchoninic acid (BCA) kit (Pierce, Rockford, Ill.). The total cellular proteins were then subjected to electrophoresis in 10% SDS/PAGE and transferred to nitrocellulose membranes. After blocking with 5% non-fat milk in a Tris-buffered saline-0.1% Tween-20 buffer (TBST), the membrane was subsequently incubated with specific primary antibodies (RORγt antibody (eBioscience, San Diego, USA) or β-actin antibody (Santa Cruz, USA)) and HRP-conjugated secondary antibodies. A chemiluminescence (ECL) detection system was used to detect the antibody-bound proteins on the membrane.

Results

Figure 3A:
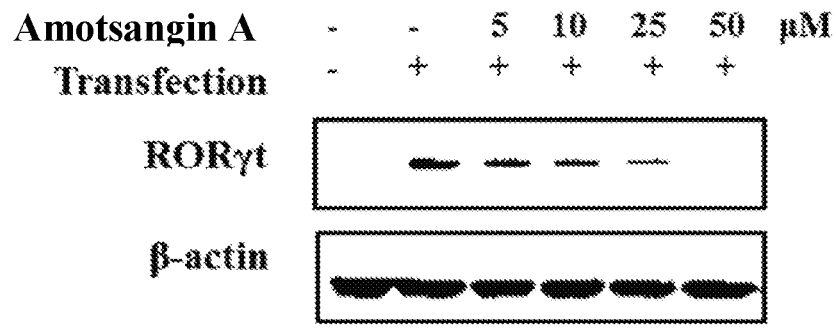
FIGS. 3A through 3D show the effect of Amotsangin A, Amotsangin B, Amotsangin C and Amotsangin D on expression of ROR-γt in ROR-γt-plasmid transfected HEK293 cells or non-transfected HEK293 cells by Western blotting analysis.
Figure 3B:
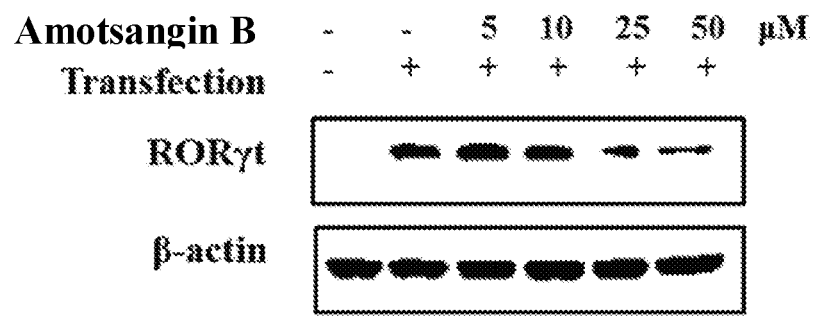
Figure 3C:
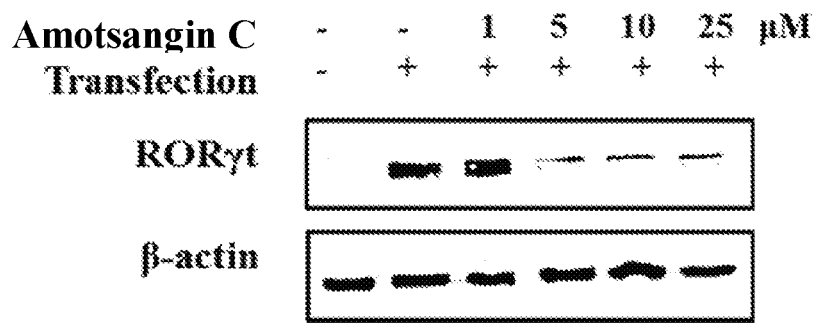
Figure 3D:
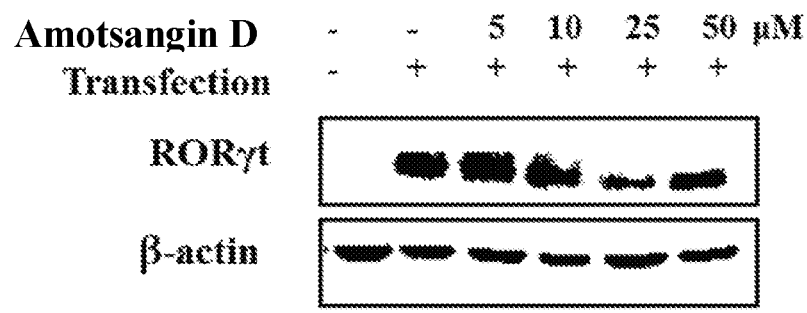

Amotsangin A dose-dependently reduced expression of ROR-γt protein when used in a concentration of from 5 to 50 μM as shown in FIG. 3A, and Amotsangin B, C and D also reduced the expression of ROR-γt protein as shown in FIG. 3B to 3D.

Example 4

Flow Cytometry Assay for the Detection of the Effects of Amotsangin A, B, C and D as Limonoids of the Present Invention on the Th17, Th1, Th2, and Treg Differentiation T Cell Differentiation Naive CD4$^+$ T cells were sorted by magnetic bead (Miltenyi Biotec) from spleen of C57BL/6 mice (8-14 weeks). CD4$^+$ T cells (5×105 cells/well) were activated with 2 μg/ml of plate-bound anti-mouse CD3 (Biolegend, San Diego, USA), and 5 μg/ml of anti-mouse CD28 (Biolegend) into 24-well-plates. For Th17 differentiation, cells were cultured for 3 days in the presence of 1 ng/ml recombinant human transforming growth factor-β (TGF-β1, Biolegend), 50 ng/ml recombinant mouse interleukin-6 (IL-6, Biolegend), and 5 ng/ml recombinant mouse IL-23 (Biolegend), and 10 μg/ml anti-mouse interleukin-4 (IL-4, Biolegend) with or without the limonoid. For the Th1 differentiation, the cells were cultured for 3 days in the presence of 2 ng/ml recombinant mouse interleukin-2 (IL-2, Biolegend), and 20 μg/ml anti-mouse IL-4 (Biolegend) with or without indicated compounds. For the Th2 differentiation, the cells were cultured for 3 days in the presence of 2 ng/ml recombinant mouse IL-2 (Biolegend), and 20 ng/ml recombinant mouse IL-4 (Biolegend), and 20 μg/ml anti-mouse IFN-γ (Biolegend) with or without compound. For the Treg differentiation, the cells were cultured for 3 days in the presence of 1 ng/ml recombinant human TGF-β1 (Biolegend), and 5 ng/ml recombinant mouse IL-2 (Biolegend) with or without indicated compounds.

Flow Cytometry

For polarization of Th17, the cells were re-stimulated in complete RPMI 1640 containing 50 ng/ml PMA, 1 μg/ml ionomycin, and 1× Brefeldin A (Biolegend) for 4 h. For polarization of Th1 and Th2, the cells were re-stimulated in complete RPMI 1640 containing 50 ng/ml PMA and 1 μg/ml ionomycin. After 1 h of incubation, 1× Monensin (Biolegend) was added and incubated for 4 h. The cells were collected and washed with Staining Buffer (BD Biosciences, New Jersey, USA), and then stained with PerCP/Cy5.5 anti-mouse CD4 (Biolegend). And then the cells were fixed for 15 min with fixation buffer (BD Biosciences), permeabilized with BD Wash buffer (1×; BD Biosciences), and stained with PE anti-mouse IL-17A (Biolegend), FITC anti-mouse IFN-γ (Biolegend), and APC anti-mouse IL-4 (Biolegend) or APC anti-mouse Foxp3 (eBioscience). The cells were analyzed by BD FACS Aria III, and the acquired data were analyzed using FlowJo software.

Results

Figure 4A:
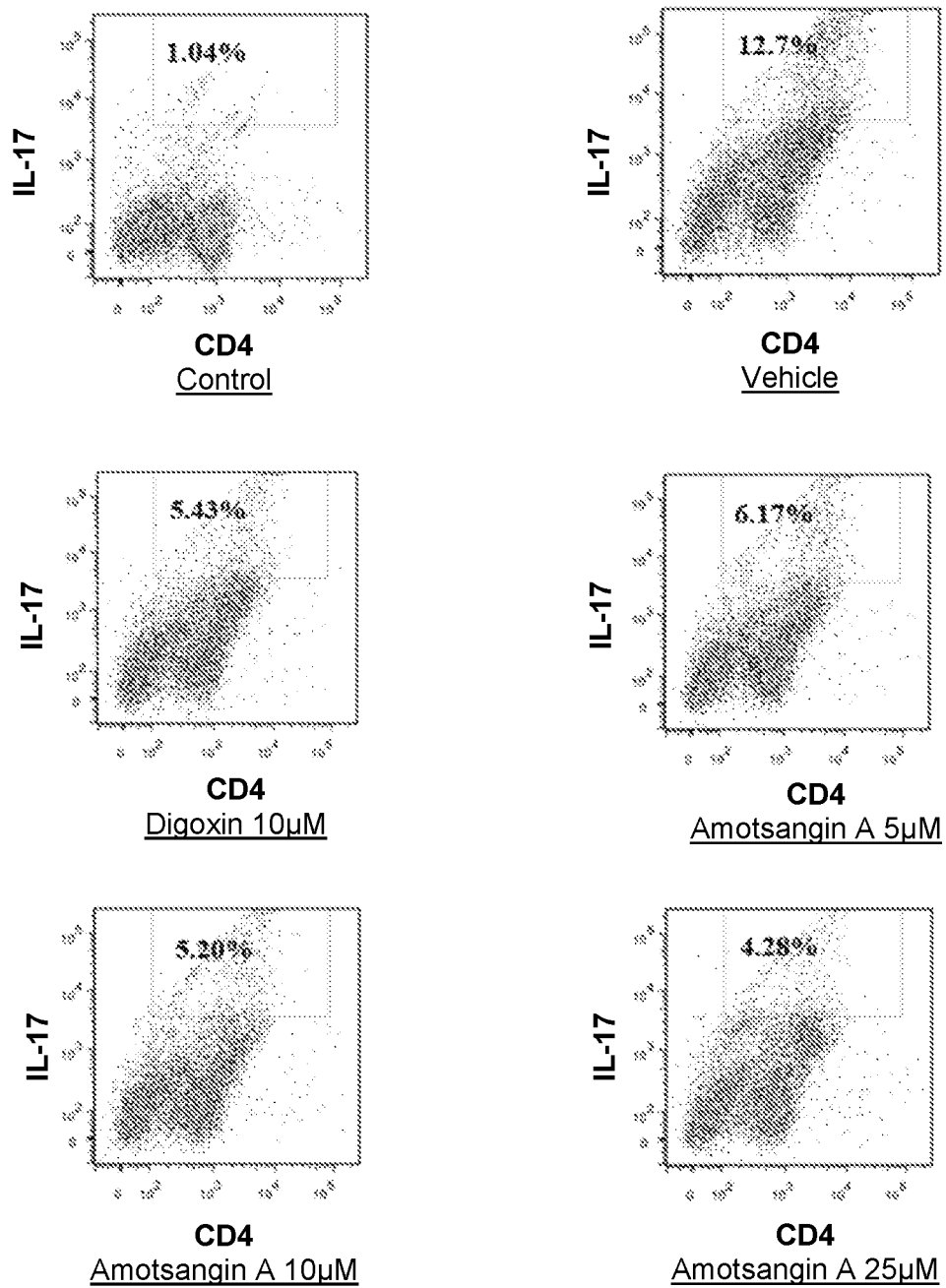
FIGS. 4A through 4H show the IL-17 production and Th17 differentiation by flow cytometry. CD4$^+$ T cells isolated from the spleens of C57BL/6 mice were cultured under Th17-polarizing conditions in the presence or absence of digoxin, or Amotsangin A, Amotsangin B, Amotsangin C or Amotsangin D at different concentrations.
Figure 4B:
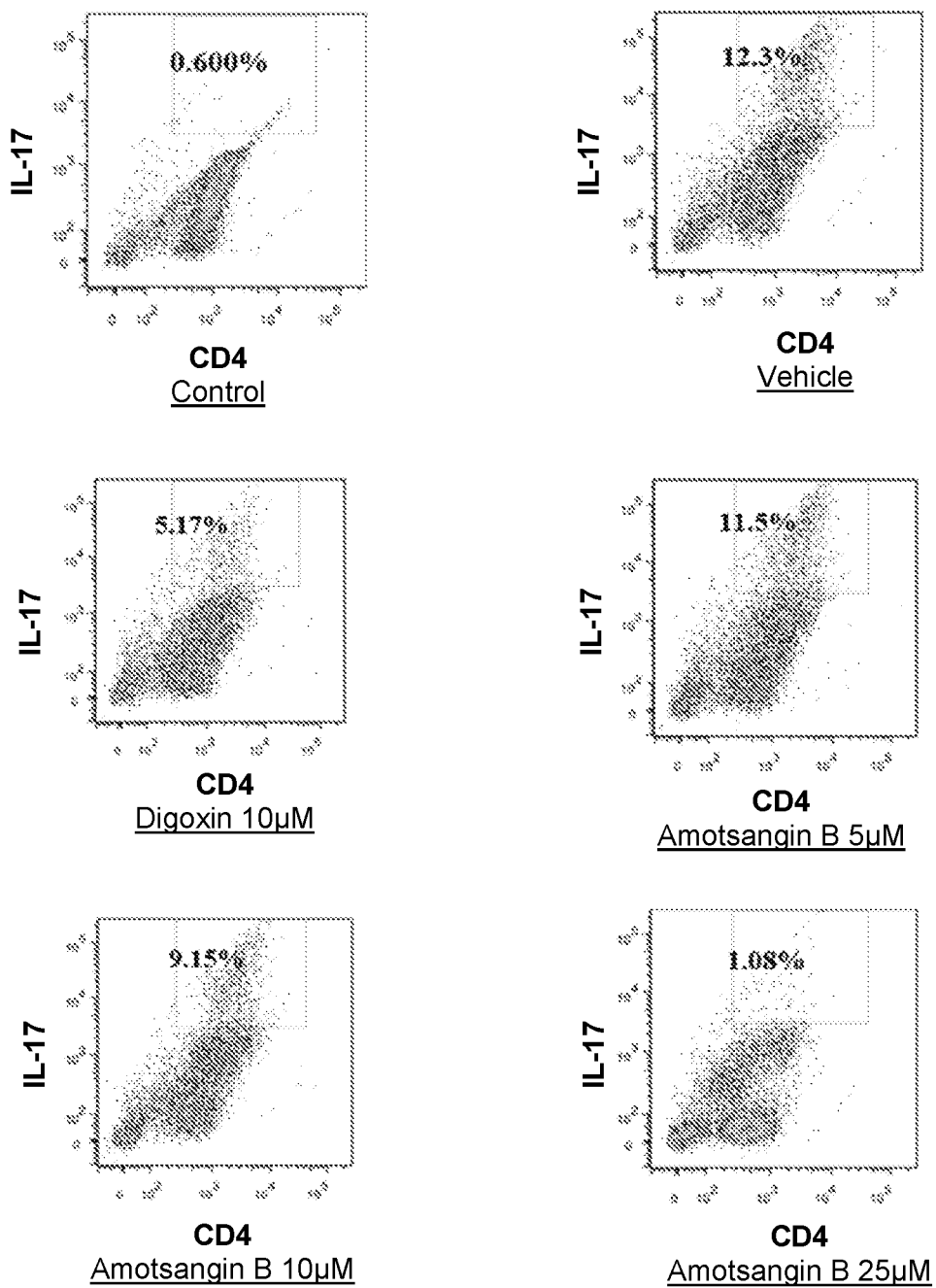
Figure 4C:
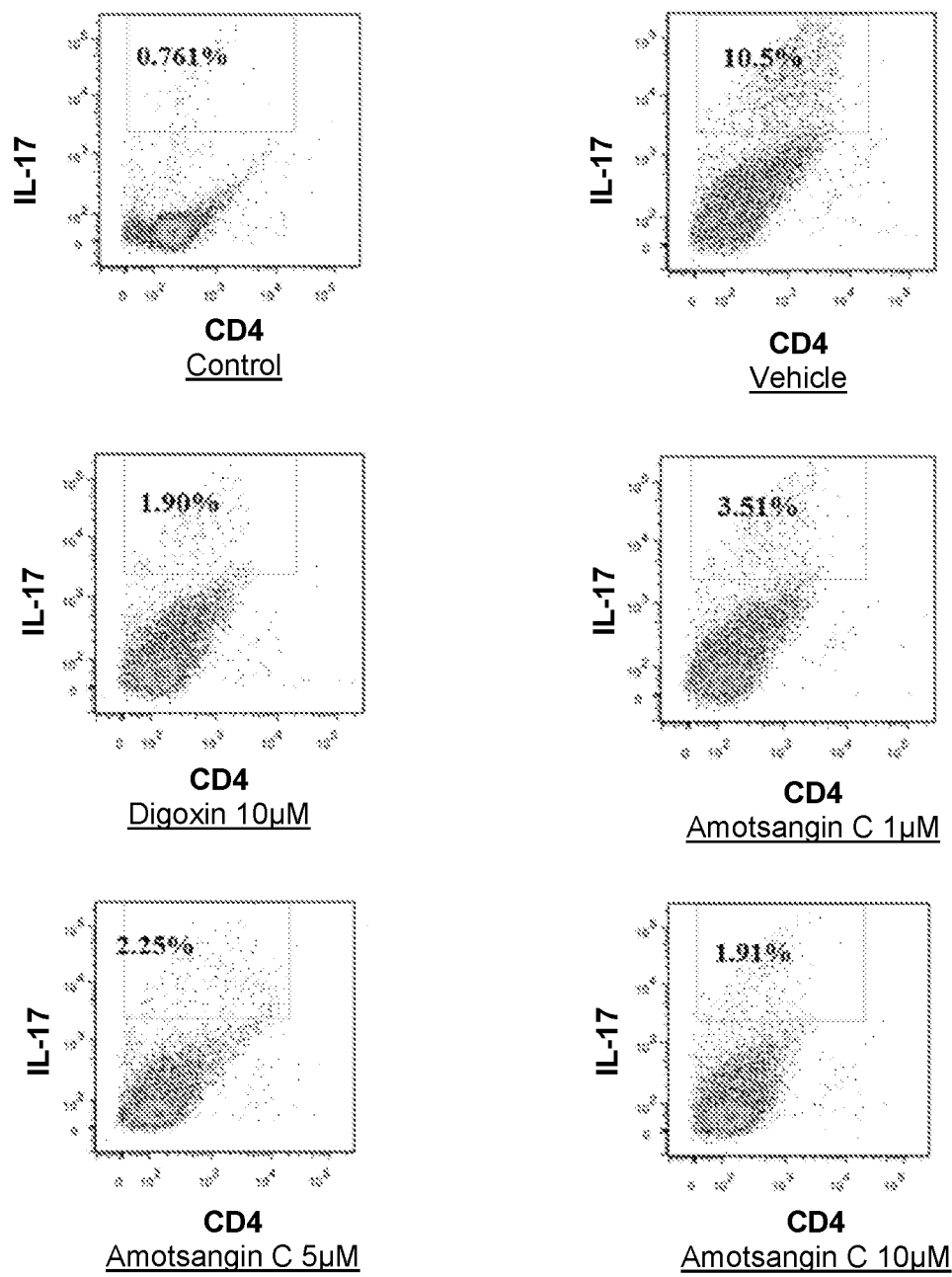
Figure 4D:
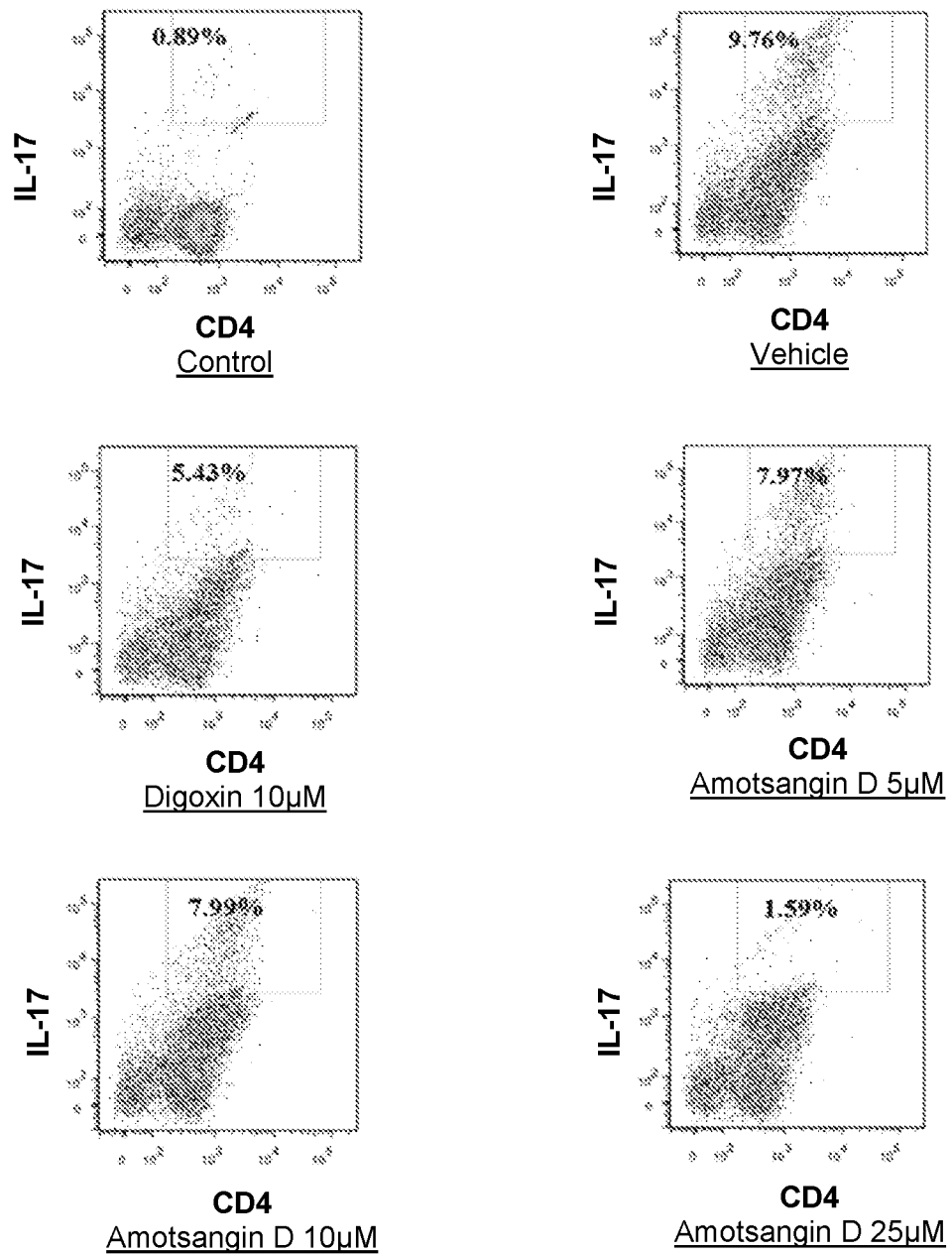
Figure 4E:
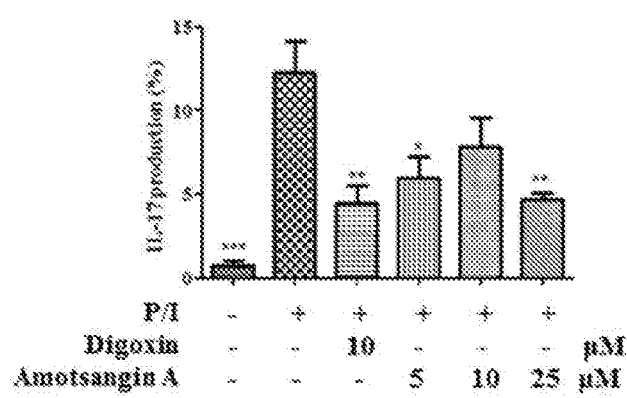
Figure 4F:
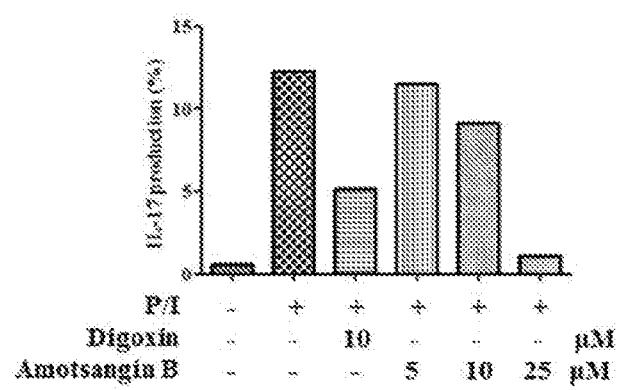
Figure 4G:
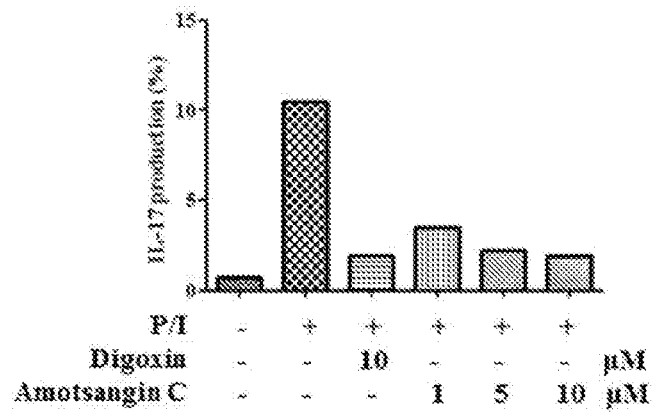
Figure 4H:
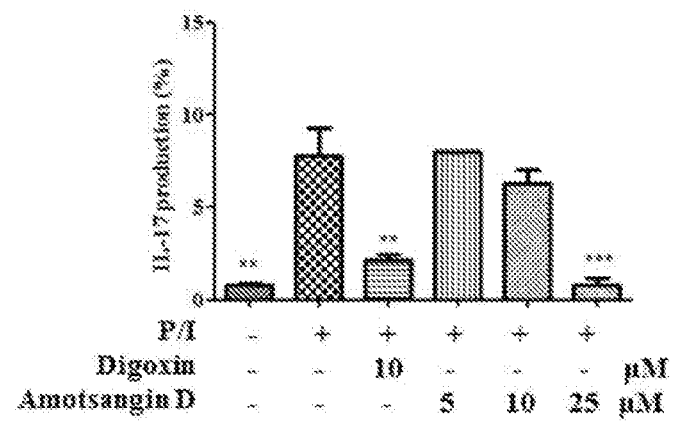

As evident from FIG. 4A, the ratio of the IL-17 production in non-treatment cells was 1.04%. In Th17-polarizing conditions, the ratio of IL-17 production was up to 12.7%, while digoxin reduced the IL-17 production to 5.43%. 25 μM Amotsangin A could reduce the ratio of the IL-17 production to 4.28%. As shown in FIG. 4B, Amotsangin B significantly reduced the ratio of the IL-17 production from 12.3% to 1.08% at 25 μM, and Amotsangin C reduced the ratio of the IL-17 production from 10.5% to 1.91% at 10 μM. Amotsangin D reduced the ratio of the IL-17 production from 9.76% to 1.59% at 25 μM (FIG. 4D). These results confirm that Amotsangin A, B, C and D can suppress the Th17 cell differentiation.

For Amotsangin A, the present invention has demonstrated that Amotsangin A inhibits ROR-γt luciferase report activity in a dose-dependent manner from 5 to 50 μM, as well as it reduces the expression of ROR-γt protein when used in a concentration of 5 to 50 μM. It is indicated that Amotsangin A can inhibit the Th17 differentiation by targeting ROR-γt. The present invention has demonstrated that Amotsangin A has no inhibitory effect on Th1, Th2 and Treg differentiation when used in a concentration of 25 μM. Amotsangin A, thus, selectively and specifically targets Th17 differentiation instead of Th1, Th2 and Treg differentiation.

For Amotsangin B, the present invention has demonstrated that Amotsangin B inhibits ROR-γt luciferase report activity in a dose-dependent manner when used in a concentration of 5 to 50 μM, as well as it reduces the expression of ROR-γt protein when used in a concentration of 5 to 50 μM. It is indicated that Amotsangin B can inhibit Th17 differentiation by suppressing ROR-γt. The present invention has demonstrated that Amotsangin B can inhibit Th1 and Th2 differentiation at 25 μM, while Amotsangin B has no effect on Treg differentiation at 25 μM. This confirms that Amotsangin B can selectively target Th17, Th1 and Th2 differentiation instead of Treg differentiation.

For Amotsangin C, the present invention has demonstrated that Amotsangin C reduces ROR-γt luciferase report activity in a dose-dependent manner when used in a concentration of 1 to 25 μM, while it also reduced expression of RORγt protein when used in a concentration of 1 to 25 μM. It is indicated that Amotsangin C inhibits Th17 differentiation by targeting ROR-γt. The present invention has demonstrated that Amotsangin C also inhibits Th1, Th2 and Treg differentiation at 10 μM.

For Amotsangin D, the present invention has demonstrated that Amotsangin D reduces ROR-γt luciferase report activity in a dose-dependent manner when used in a concentration of 5 to 50 μM, while it also reduces the expression of ROR-γt protein when used in a concentration of 5 to 50 μM. It is indicated that Amotsangin C inhibits Th17 differentiation by targeting ROR-γt. The present invention has demonstrated that Amotsangin D could inhibit Th2 differentiation, and Amotsangin D has no inhibitory effect on Th1 and Treg differentiation when used in a concentration of 25 μM.

Figure 5A:
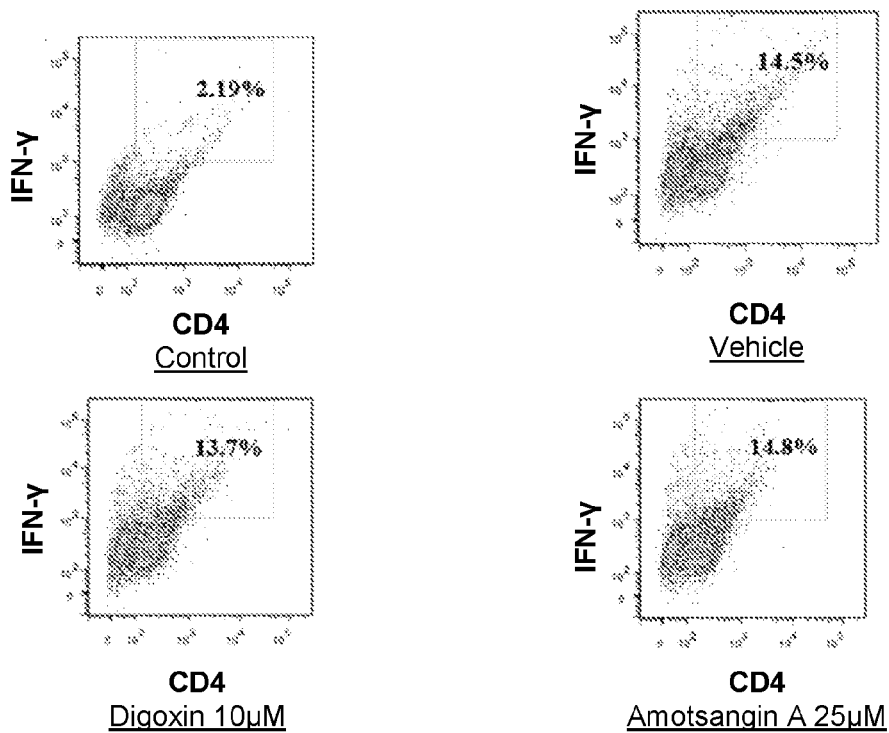
FIGS. 5A through 5H show the IFN-γ production and Th1 differentiation by flow cytometry. CD4$^+$ T cells isolated from the spleens of C57BL/6 mice were cultured under Th1-polarizing conditions in the presence or absence of digoxin, or Amotsangin A, Amotsangin B, Amotsangin C or Amotsangin D.
Figure 5B:
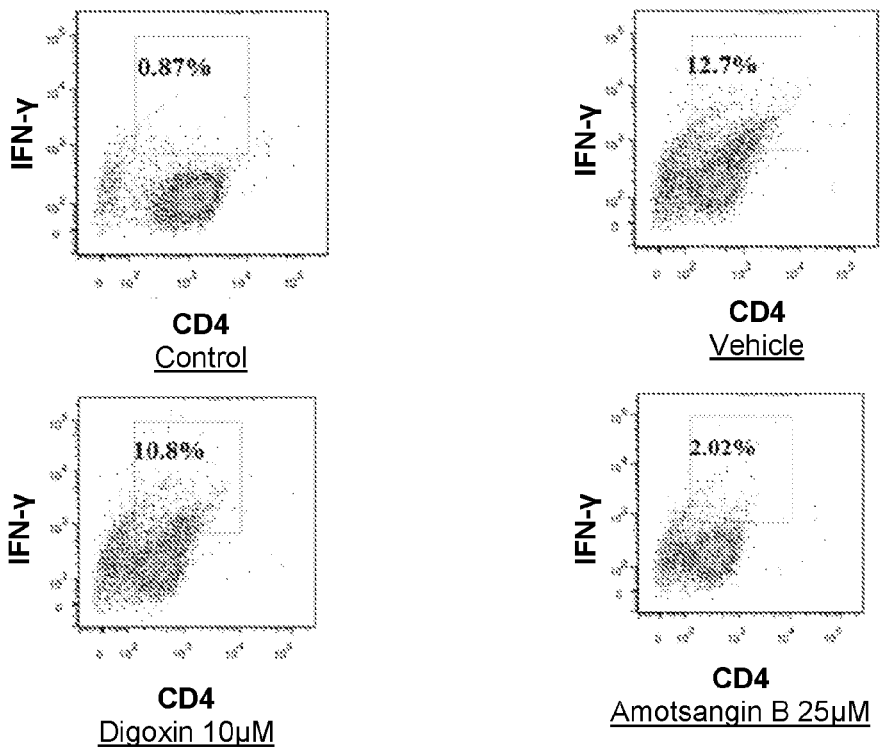
Figure 5C:
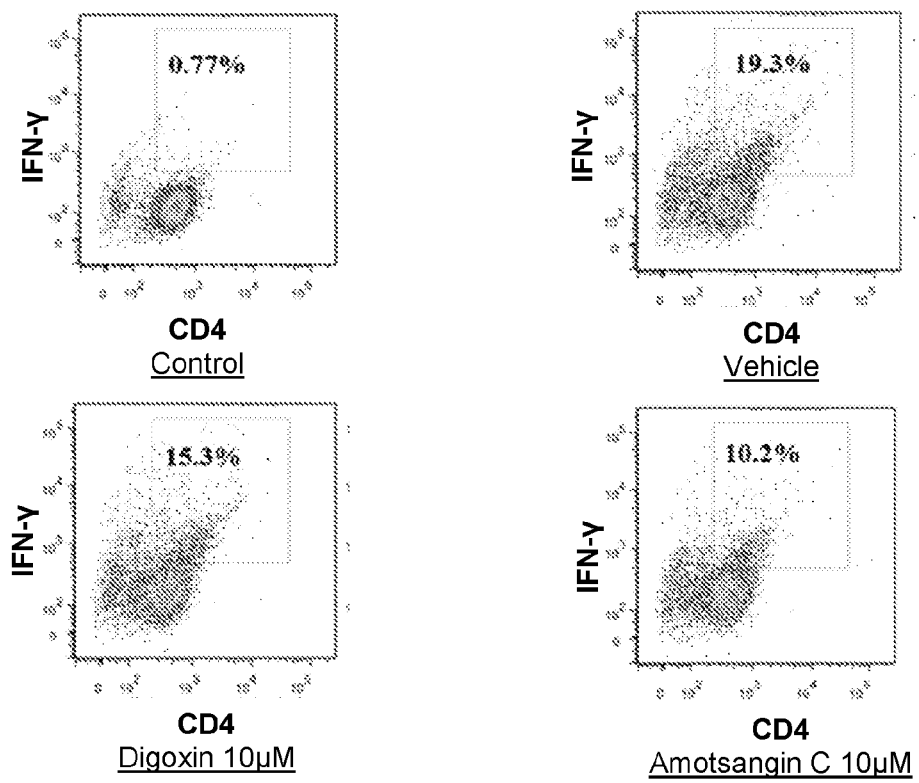
Figure 5D:
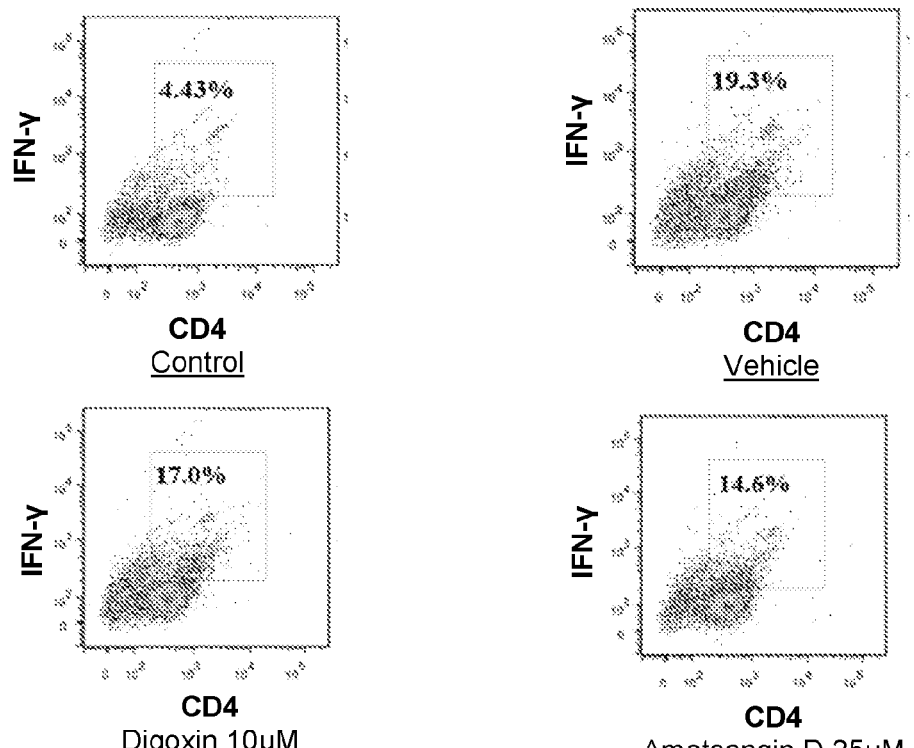
Figure 5E:
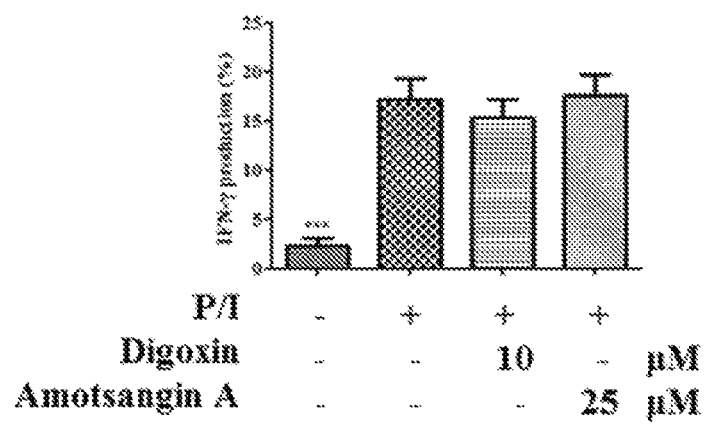
Figure 5F:
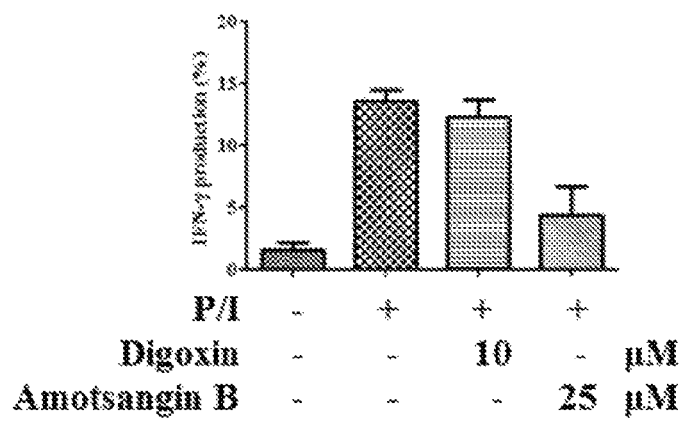
Figure 5G:
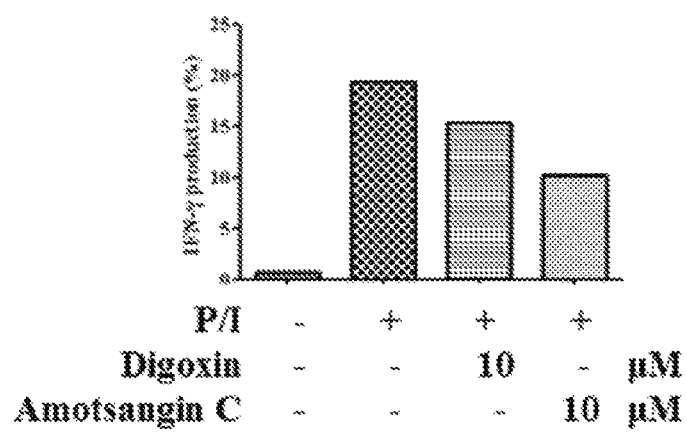
Figure 5H:
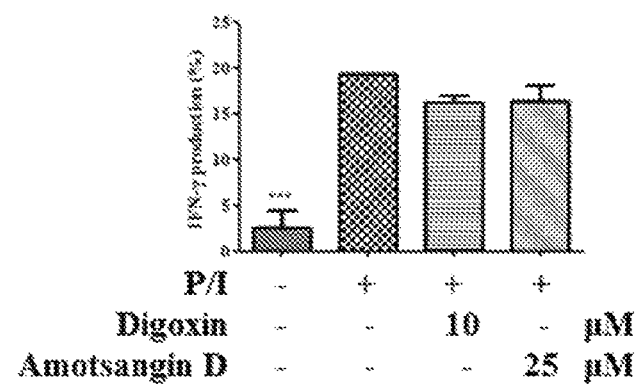

As shown in FIG. 5A, when the cells were treated with Amotsangin A, the ratio of IFN-γ producing Th1 differentiation could not be changed. It suggested that Amotsangin A has no effect on the Th1 cell differentiation. As shown in FIG. 5B, Amotsangin B could attenuate the ratio of the IFN-γ producing Th1 differentiation from 12.7% to 2.02%, while digoxin gave 10.8%, suggesting that Amotsangin B can inhibit Th1 cell differentiation. As shown in FIG. 5C, Amotsangin C can change the ratio of the IFN-γ producing Th1 differentiation from 19.3% to 10.2%, while the result with digoxin was 15.3%. This suggests that Amotsangin C can inhibit the Th1 cell differentiation. As shown in FIG. 5D, Amotsangin D can change the ratio of the IFN-γ producing Th1 differentiation from 19.3% to 14.6%, while the result with digoxin was 17.0%. This suggests that Amotsangin D has a slight inhibitory effect on the Th1 cell differentiation compared to digoxin.

Figure 6A:
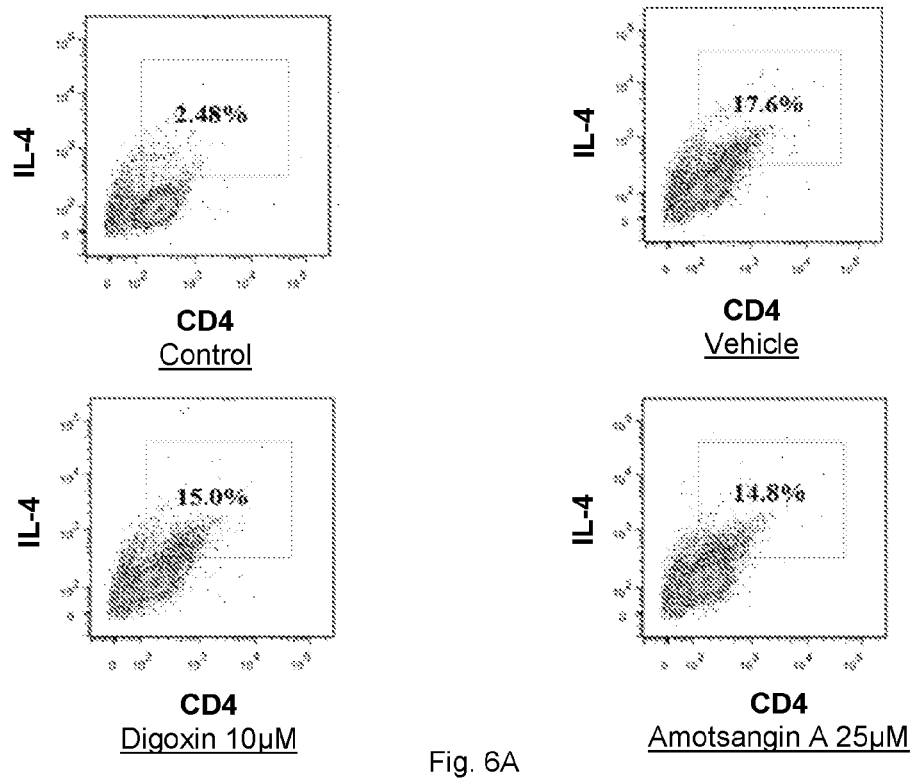
Figure 6B:
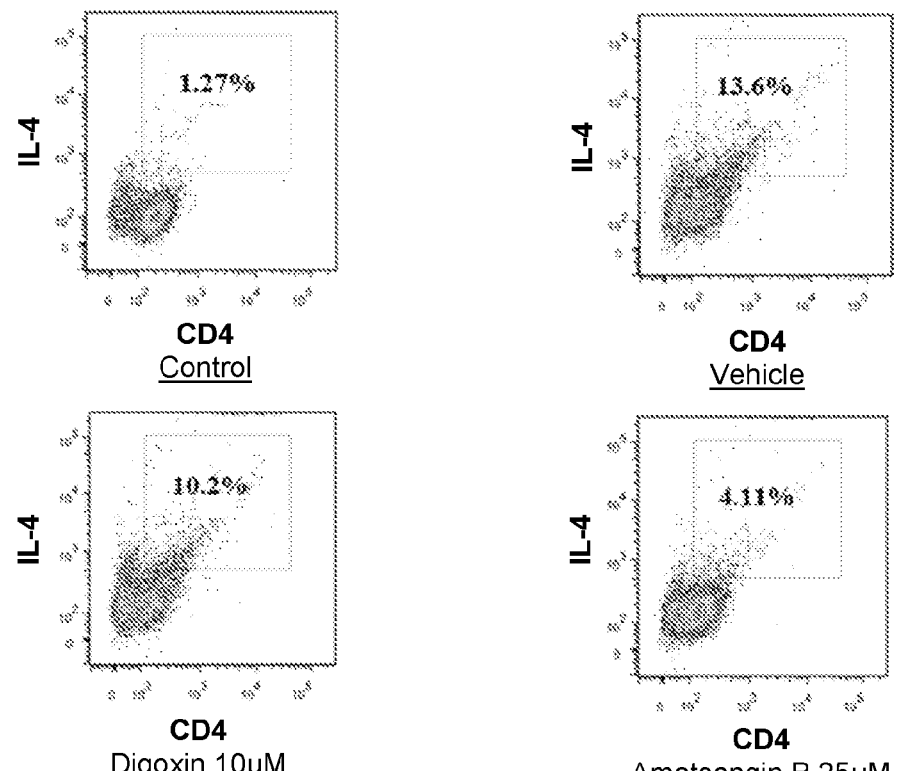
Figure 6E:
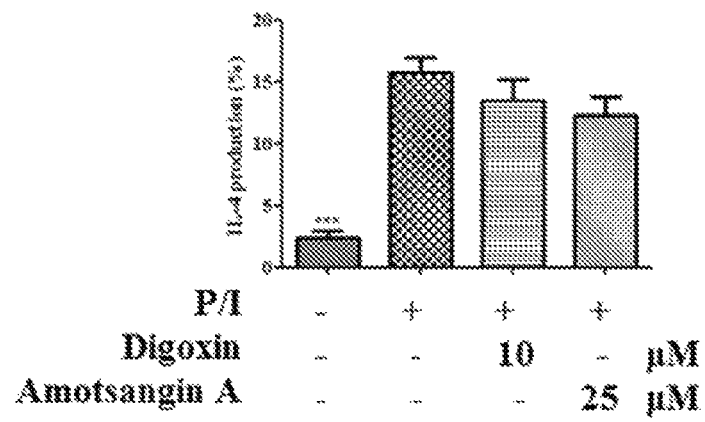
Figure 6F:
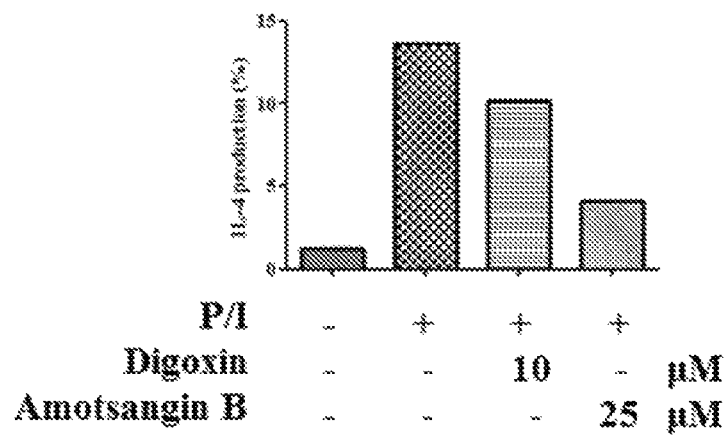
Figure 6G:
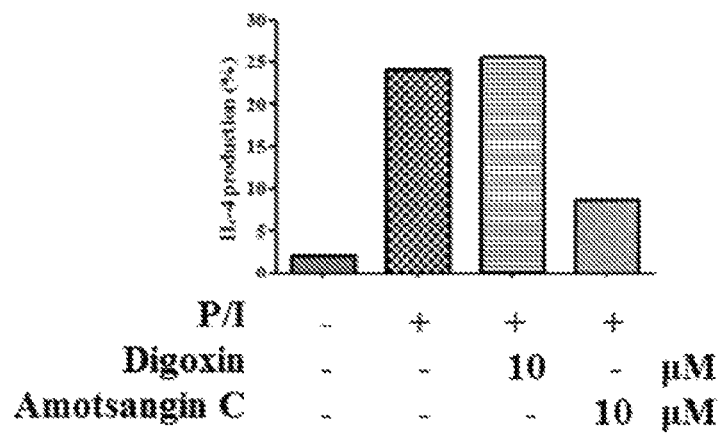
Figure 6H:
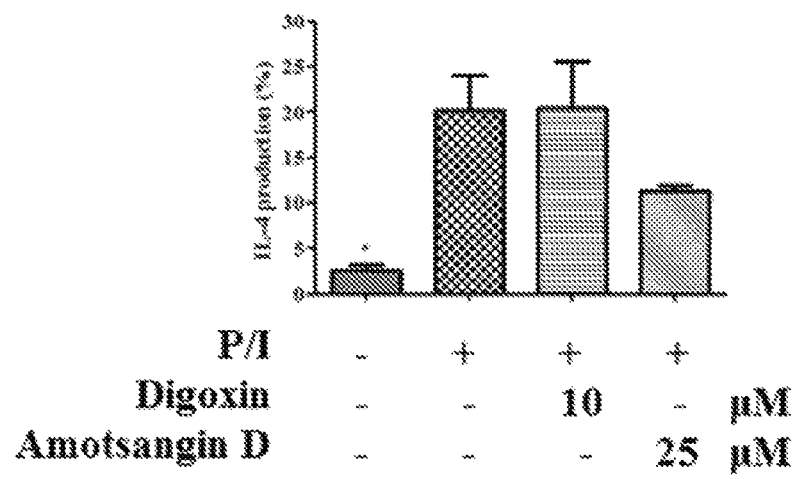

Regarding the effects of these compounds on the Th2 polarization, when the cells were incubated with Amotsangin A, the ratio of the IL-4 producing Th2 differentiation changed from 17.6% to 14.8%, while the ratio of the cells treated with digoxin was 15.0%. This suggests that Amotsangin A has no effect on the Th2 cell differentiation (FIG. 6A). As shown in FIG. 6B, Amotsangin B could decrease the ratio of the IL-4 producing Th2 differentiation from 13.6% to 4.11%, while digoxin gave 10.2%, indicating that Amotsangin B can inhibit the Th2 cell differentiation. Additionally, Amotsangin C can inhibit the ratio of the IL-4 producing Th2 differentiation from 24.1% to 8.7% (FIG. 6C). Furthermore, Amotsangin D slightly reduced the ratio of the IL-4 producing Th2 differentiation from 16.2% to 11.9%.

Figure 7A:
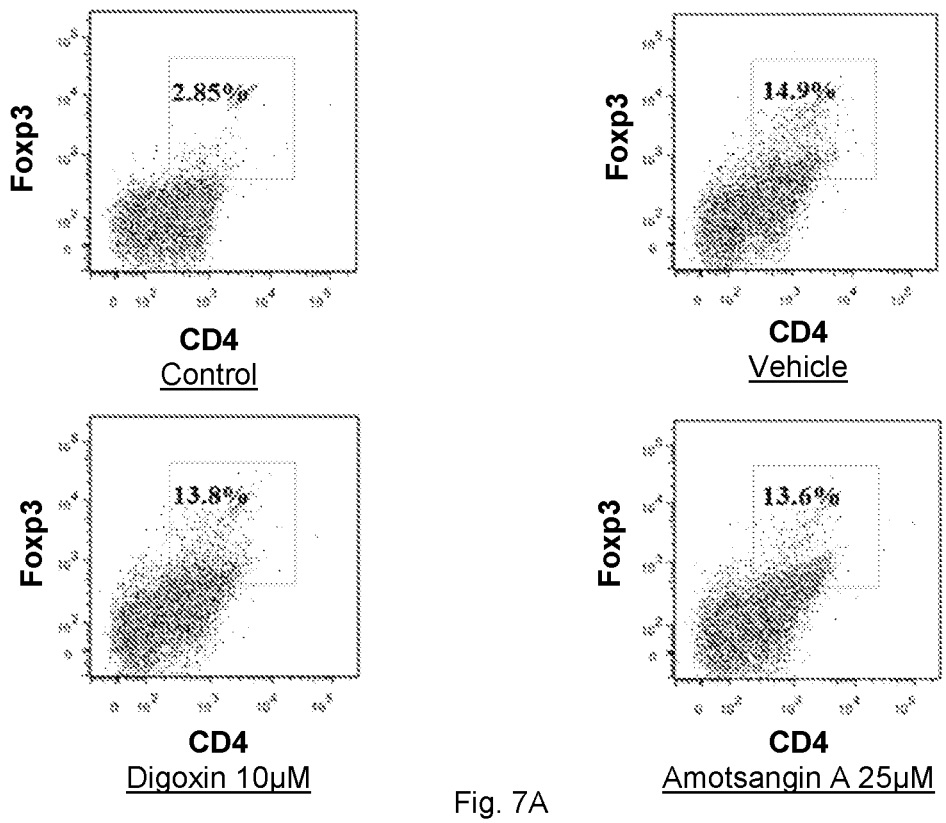
FIGS. 7A through 7H show the Foxp3 production and Treg differentiation by flow cytometry. CD4+ T cells isolated from the spleens of C57BL/6 mice were cultured under Treg-polarizing conditions in the presence or absence of digoxin, or Amotsangin A, Amotsangin B, Amotsangin C or Amotsangin D.
Figure 7B:
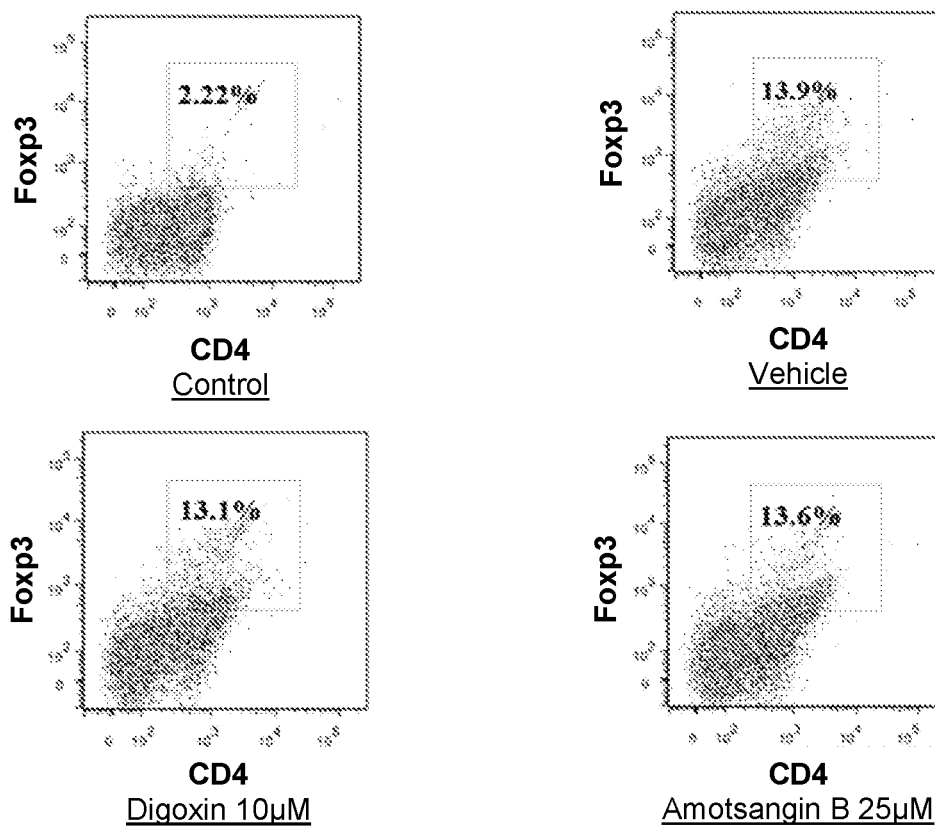
Figure 7C:
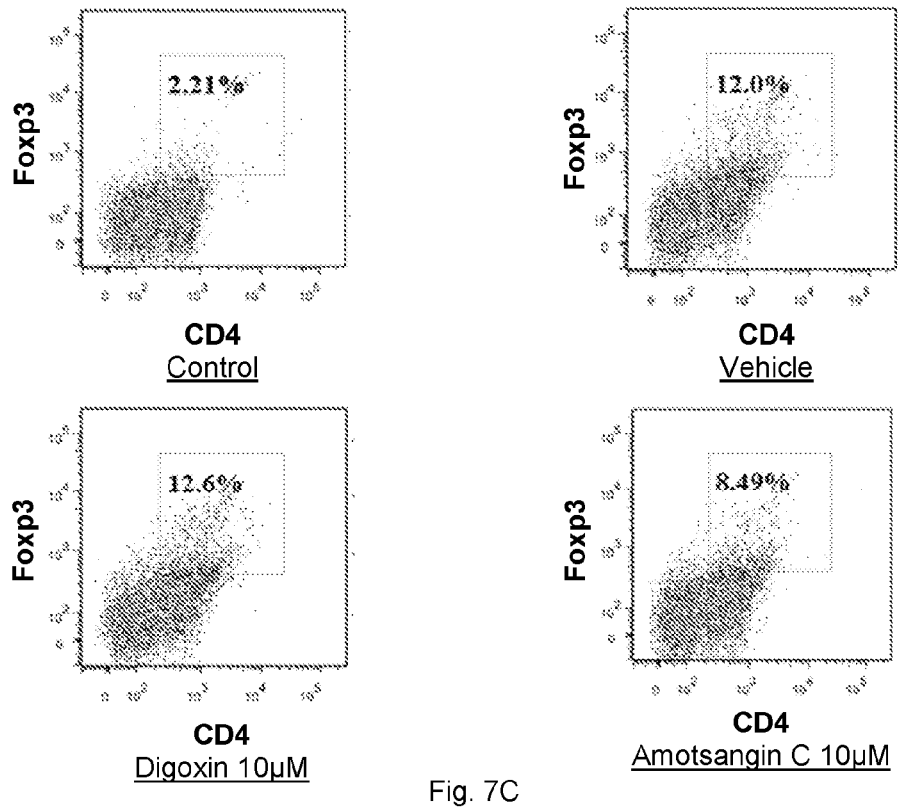
Figure 7D:
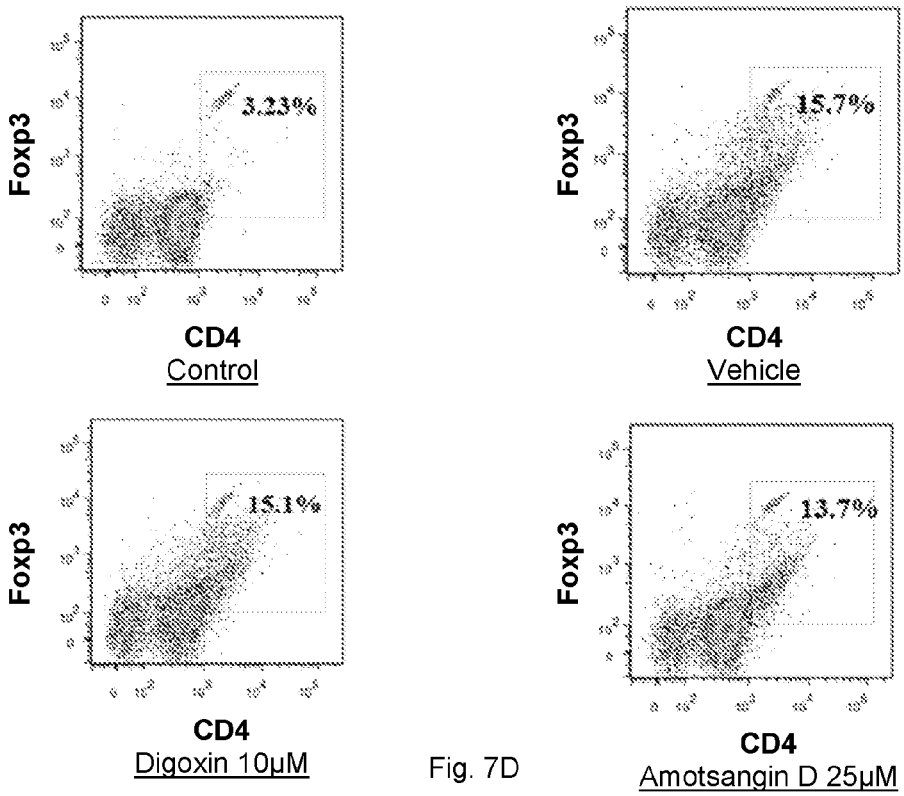
Figure 7E:
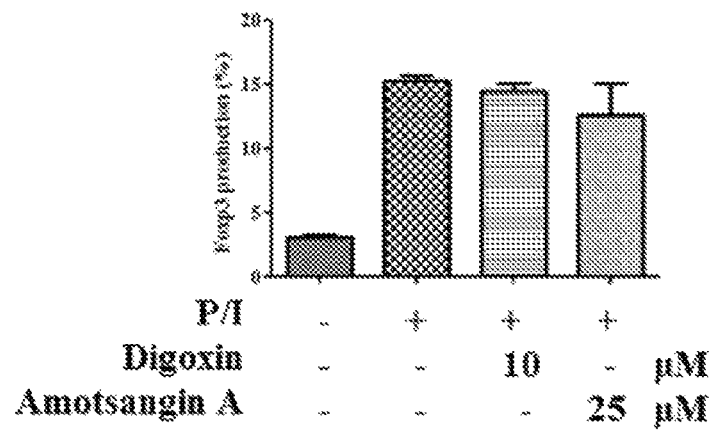
Figure 7F:
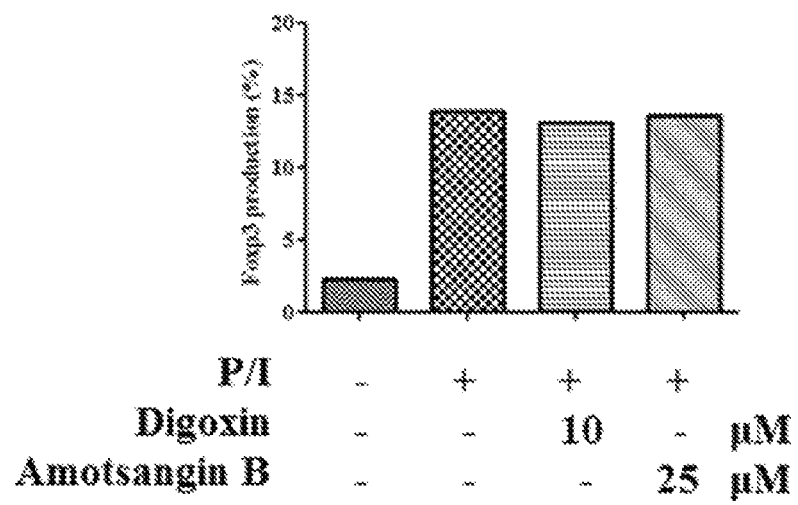
Figure 7G:
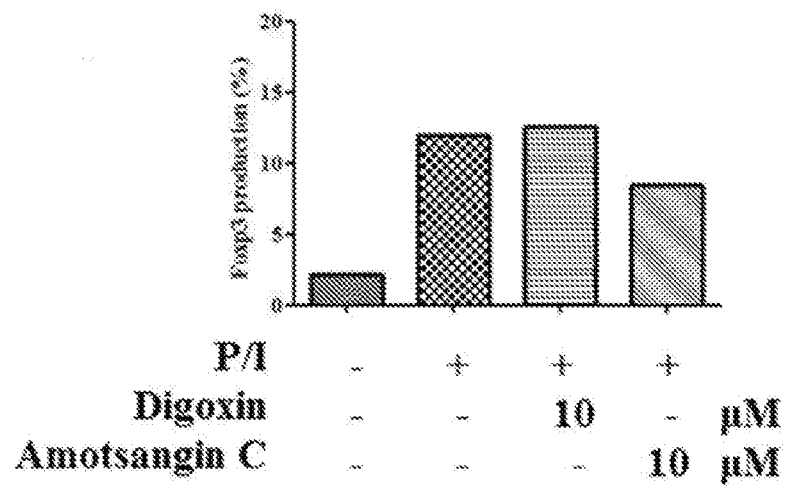
Figure 7H:
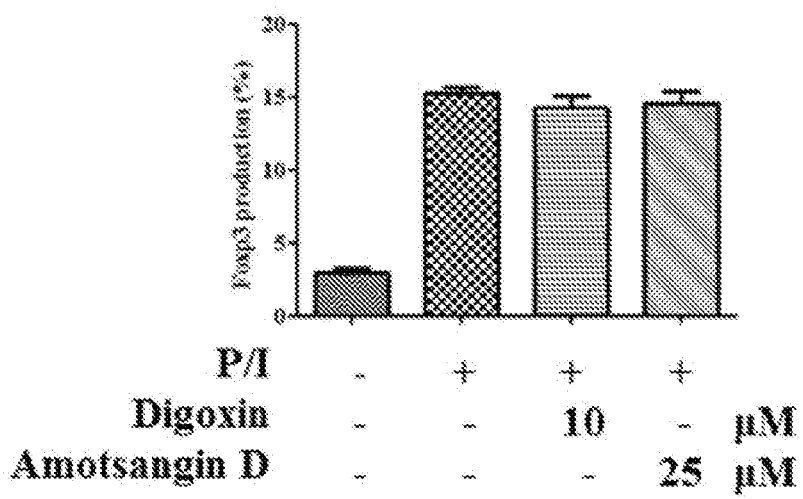

As shown in FIG. 7A, Amotsangin A has not obvious effect on the Foxp3 producing Treg differentiation, suggesting that Amotsangin A has no effect on the Treg cell differentiation and selectively inhibits Th17 polarization. Similarly, Amotsangin B has not effect on Treg differentiation (FIG. 7B), Although these compound share a similar chemical structure, Amotsangin C significantly inhibited Treg differentiation from 12.0% to 8.49% (FIG. 7C). As shown in FIG. 7D, Amotsangin D slightly inhibited the Treg differentiation from 15.7% to 13.7%.

The invention claimed is:

1. A method of treating a subject suffering from an autoimmune disease comprising administering an effective amount of a limonoid to said subject, wherein the limonoid comprises a structure of Formula (I):

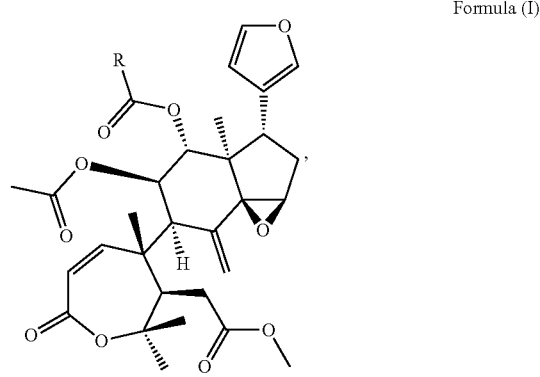

Formula (I)

wherein R is selected from an optionally hydroxylated alkyl group.

2. The method of claim 1, wherein R is selected from an optionally hydroxylated $C_1$-$C_5$ alkyl group.

3. The method of claim 1, wherein R is selected from one of ethyl, 2-butyl, iso-propyl or 1-hydroxy-2-methyl-butyl.

4. The method of claim 1, wherein the limonoid comprises a structure selected from one of Formulas (II) to (V):

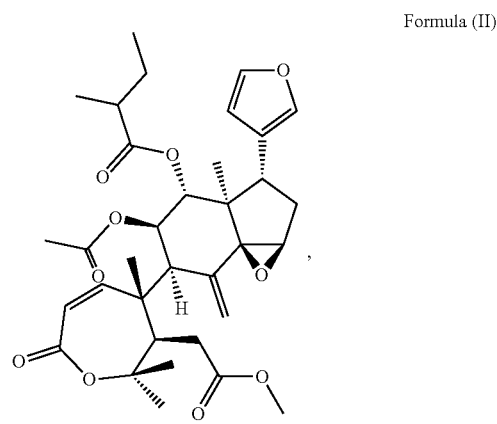

Formula (II)

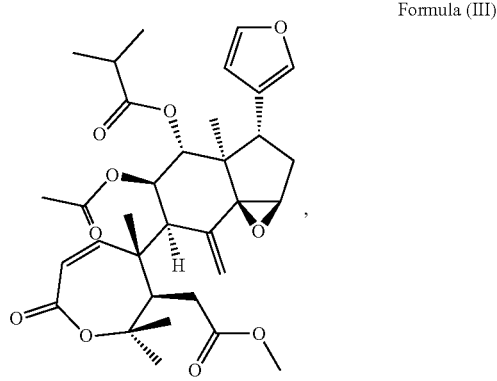

Formula (III)

-continued

Formula (IV)

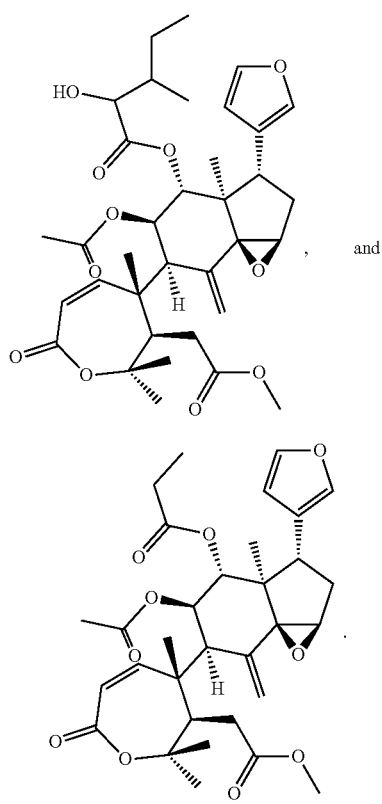

and

Formula (V)

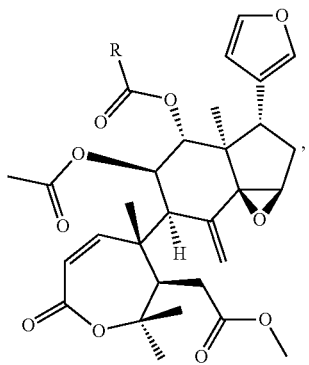

5. The method of claim 1, wherein the autoimmune disease is selected from systemic lupus erythematosus, multiple sclerosis or rheumatoid arthritis and wherein the subject is a human.

6. The method of claim 1, wherein the limonoid inhibits the T helper 17 cell differentiation.

7. The method of claim 1, wherein the limonoid reduces the retinoic acid-related orphan nuclear receptor γt (ROR-γt) protein expression.

8. The method of claim 1, wherein the limonoid reduces the interleukin 17 (IL-17) production.

9. A method of inhibiting the differentiation of T helper 17 cells comprising contacting naive CD4⁺ T cells with an effective amount of a limonoid, wherein the limonoid comprises a structure of Formula (I):

Formula (I)

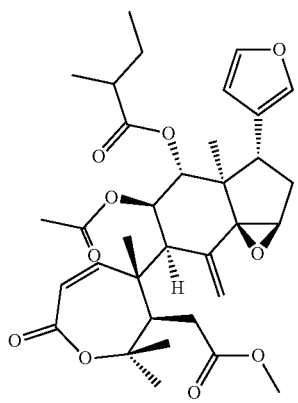

wherein R is selected from an optionally hydroxylated alkyl group.

10. The method of claim 9, wherein the limonoid reduces the retinoic acid-related orphan nuclear receptor γt (ROR-γt) protein expression.

11. The method of claim 9, wherein the limonoid reduces the interleukin 17 (IL-17) production.

12. The method of claim 9, wherein the effective amount means a concentration of the limonoid of about 1 μM to about 50 μM.

13. The method of claim 9, wherein the limonoid comprises a structure selected from one of Formulas (II) to (V):

Formula (II)

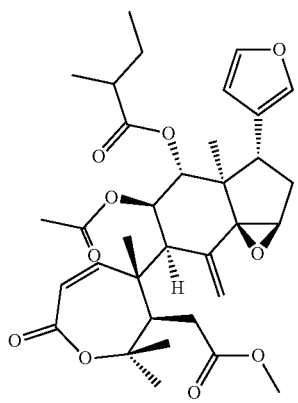

Formula (III)

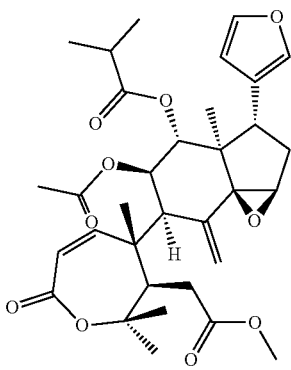

Formula (IV)

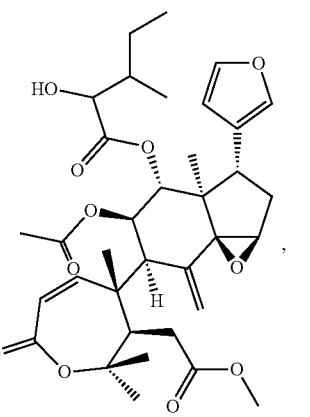

and

Formula (V)

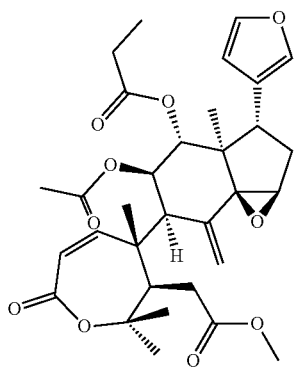

14. The method of claim 9, wherein the limonoid comprises a structure of Formula (II):

Formula (II)

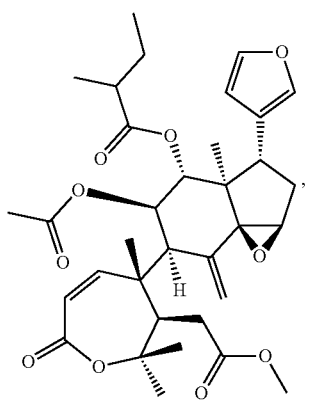

and wherein the limonoid is used in a concentration of between about 5 μM and about 50 μM.

15. A method of inhibiting the differentiation of one or more of T helper 1 cells, T helper 2 cells or regulatory T cells comprising contacting naive CD4+ T cells with an effective amount of a limonoid, wherein the limonoid comprises a structure of Formula (I):

Formula (I)

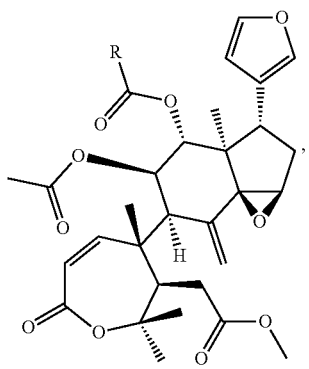

wherein R is selected from an optionally hydroxylated alkyl group.

16. The method of claim 15, wherein the limonoid reduces one or more of the INF-γ production, the IL-4 production or the Foxp3 production.

17. The method of claim 15, wherein the differentiation of the T helper 1 cells is inhibited and wherein the limonoid comprises a structure of one of Formulas (III) or (IV):

Formula (III)

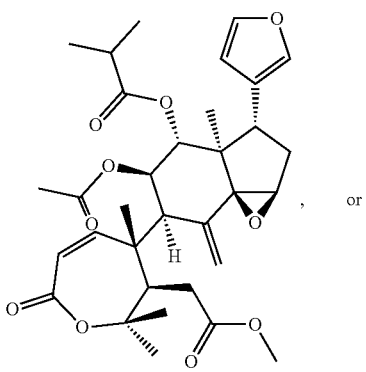

, or

Formula (IV)

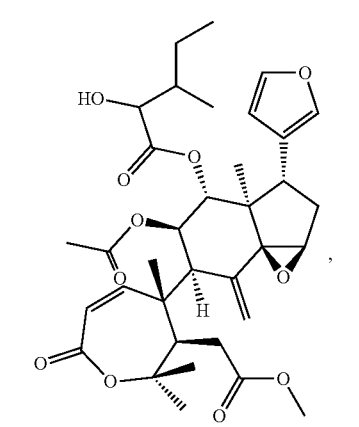

, and wherein the limonoid is used in a concentration of about 10 μM to about 25 μM.

18. The method of claim 15, wherein the differentiation of the T helper 2 cells is inhibited and wherein the limonoid comprises a structure of one of Formulas (III), (IV) or (V):

Formula (III)

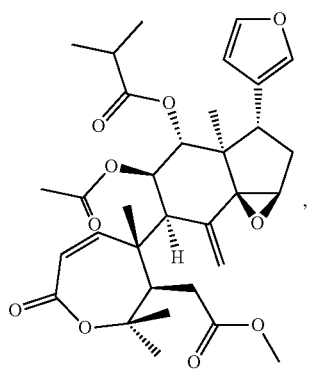

,

-continued
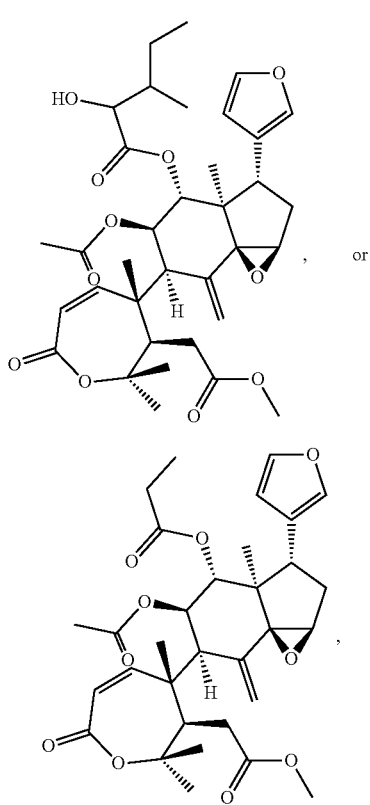
Formula (V)
and wherein the limonoid is used in a concentration of between about 10 μM and about 25 μM.
19. The method of claim 15, wherein the differentiation of the regulatory T cells is inhibited and wherein the limonoid comprises a structure of Formula (IV)
Formula (IV)
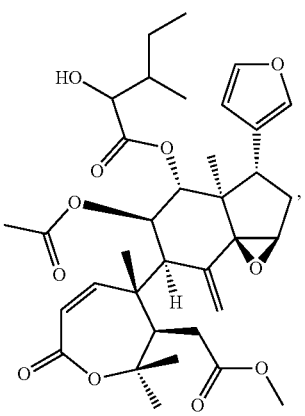
and wherein the limonoid is used in a concentration of about 10 μM.
* * * * *